US010716521B2

(12) United States Patent
Van De Rijdt et al.

(10) Patent No.: US 10,716,521 B2
(45) Date of Patent: Jul. 21, 2020

(54) PATIENT SUPPORT SYSTEM AND LEVELLING SYSTEM FOR SUCH A PATIENT SUPPORT SYSTEM

(71) Applicant: FRENCKEN EUROPE B.V., Eindhoven (NL)

(72) Inventors: Johannes Hubertus Antonius Van De Rijdt, Eindhoven (NL); Mark Antonius Adriana Van Den Akker, Eindhoven (NL); Peter Van Der Krieken, Eindhoven (NL); Ton Antonius Cornelis Henricus Kluijtmans, Eindhoven (NL); Lucas Hendricus Johannes Donker, Eindhoven (NL)

(73) Assignee: Frencken Europe B.V., Eindhoven (NL)

( * ) Notice: Subject to any disclaimer, the term of this patent is extended or adjusted under 35 U.S.C. 154(b) by 364 days.

(21) Appl. No.: 15/321,514

(22) PCT Filed: Jun. 25, 2015

(86) PCT No.: PCT/NL2015/050464
§ 371 (c)(1),
(2) Date: Dec. 22, 2016

(87) PCT Pub. No.: WO2015/199540
PCT Pub. Date: Dec. 30, 2015

(65) Prior Publication Data
US 2017/0156684 A1 Jun. 8, 2017

(30) Foreign Application Priority Data

Jun. 26, 2014 (NL) ..................................... 2013067
Jun. 26, 2014 (NL) ..................................... 2013068

(Continued)

(51) Int. Cl.
A61B 6/04 (2006.01)
A61G 13/04 (2006.01)
A61B 6/00 (2006.01)

(52) U.S. Cl.
CPC .............. *A61B 6/0457* (2013.01); *A61B 6/04* (2013.01); *A61B 6/5276* (2013.01); *A61G 13/04* (2013.01);
(Continued)

(58) Field of Classification Search
CPC ....... A61B 6/04; A61B 6/0407; A61B 6/0457; A61B 6/5276; A61G 13/02; A61G 13/04;
(Continued)

(56) References Cited

U.S. PATENT DOCUMENTS

| 5,237,600 A * | 8/1993 | Kamata ................ A61B 6/0457 378/177 |
| 5,386,453 A * | 1/1995 | Harrawood .......... A61B 6/0442 378/193 |

(Continued)

FOREIGN PATENT DOCUMENTS

| EP | 2399521 A1 * | 12/2011 | ........... A61B 5/6887 |
| JP | 1992111311 | 9/1992 | |

(Continued)

OTHER PUBLICATIONS

Office Action from related Japanese Patent Application No. 2017-520854, dated Dec. 19, 2018, 5 pages (English translation only).

*Primary Examiner* — David R Hare
(74) *Attorney, Agent, or Firm* — Quarles & Brady LLP

(57) ABSTRACT

The current invention relates to a patient support table, comprising a frame that is mounted to the floor, an upright column with a table top support system and mounted to the frame and supporting a table top that is movable longitudinally with respect to the column and to accommodate a (Continued)

person. The patient table further comprises a tilt actuator and a control device to control the at least one tilt actuator, and comprising an inclinometer, a data storage and a processing unit that in use compares data from the inclinometer with data from the data storage. The control device comprises a force sensor to determine a load supported by the table top and/or a position sensor to determine the longitudinal position of the table top with respect to a reference, wherein the control device in use calculates a set point for the at least one tilt actuator and actuates the tilt actuator to move or maintain the table top to the set tilted position. The invention also relates to a control device and to the use van such a control device and/or such a patient table.

11 Claims, 11 Drawing Sheets

(30) Foreign Application Priority Data

| Jun. 26, 2014 | (NL) | ..................................... | 2013069 |
| Jun. 26, 2014 | (NL) | ..................................... | 2013070 |
| Jun. 26, 2014 | (NL) | ..................................... | 2013071 |

(52) U.S. Cl.
CPC ...... *A61G 2203/10* (2013.01); *A61G 2203/32* (2013.01); *A61G 2203/40* (2013.01); *A61G 2203/42* (2013.01); *A61G 2203/44* (2013.01); *A61G 2210/50* (2013.01)

(58) Field of Classification Search
CPC ............ A61G 2203/10; A61G 2203/32; A61G 2203/40; A61G 2203/42; A61G 2203/44; A61G 2210/50
See application file for complete search history.

(56) References Cited

U.S. PATENT DOCUMENTS

| 6,334,708 | B1* | 1/2002 | Kosugi | ............... | A61B 6/0457 378/197 |
| 6,574,808 | B1* | 6/2003 | Brown | ................ | A61B 6/0457 5/601 |
| 6,651,279 | B1* | 11/2003 | Muthuvelan | ......... | A61B 6/0457 5/600 |
| 7,029,175 | B2* | 4/2006 | Karaus | ................... | A61B 6/102 378/197 |
| 7,065,813 | B2* | 6/2006 | Hoth | .................... | A61B 6/0457 378/209 |
| 8,764,291 | B2* | 7/2014 | Ruijters | ................ | A61B 5/06 378/195 |
| 2002/0081008 | A1* | 6/2002 | Wollenweber | ........... | A61B 6/04 382/131 |
| 2002/0120986 | A1* | 9/2002 | Erbel | .................... | A61B 6/0421 5/601 |
| 2002/0122575 | A1* | 9/2002 | Vaisburd | .................. | A61B 6/04 382/131 |
| 2004/0028188 | A1* | 2/2004 | Amann | ................ | A61B 6/0457 378/209 |
| 2004/0046668 | A1* | 3/2004 | Smith | .................... | A61B 5/1115 340/573.7 |
| 2004/0057557 | A1* | 3/2004 | Nafstadius | ............... | A61B 6/04 378/209 |
| 2004/0172756 | A1* | 9/2004 | Somasundaram | ... | A61B 6/0457 5/600 |
| 2004/0172757 | A1* | 9/2004 | Somasundaram | ..... | A61B 6/105 5/601 |
| 2004/0172758 | A1* | 9/2004 | Alakkat | ................... | A61B 6/04 5/610 |
| 2006/0193443 | A1* | 8/2006 | Reger | .................. | A61B 5/0555 378/207 |
| 2007/0003020 | A1* | 1/2007 | Hsieh | ..................... | A61B 6/032 378/207 |
| 2008/0289106 | A1* | 11/2008 | Beyer | ................... | A61B 6/0457 5/601 |
| 2011/0296613 | A1* | 12/2011 | Farmbauer | ........... | A61B 5/0555 5/600 |
| 2012/0106701 | A1* | 5/2012 | Meek | ................... | A61B 6/4482 378/62 |
| 2012/0114107 | A1* | 5/2012 | Wang | .................... | A61B 5/704 378/209 |
| 2014/0051964 | A1* | 2/2014 | Hori | ..................... | A61B 6/0457 600/407 |
| 2014/0334608 | A1* | 11/2014 | Mulzer | ................... | A61B 6/04 378/207 |

FOREIGN PATENT DOCUMENTS

| JP | 2004180846 | 7/2004 |
| JP | 2006-110233 | 4/2006 |
| JP | 2008142260 | 6/2008 |
| JP | 2011072327 | 4/2011 |

* cited by examiner

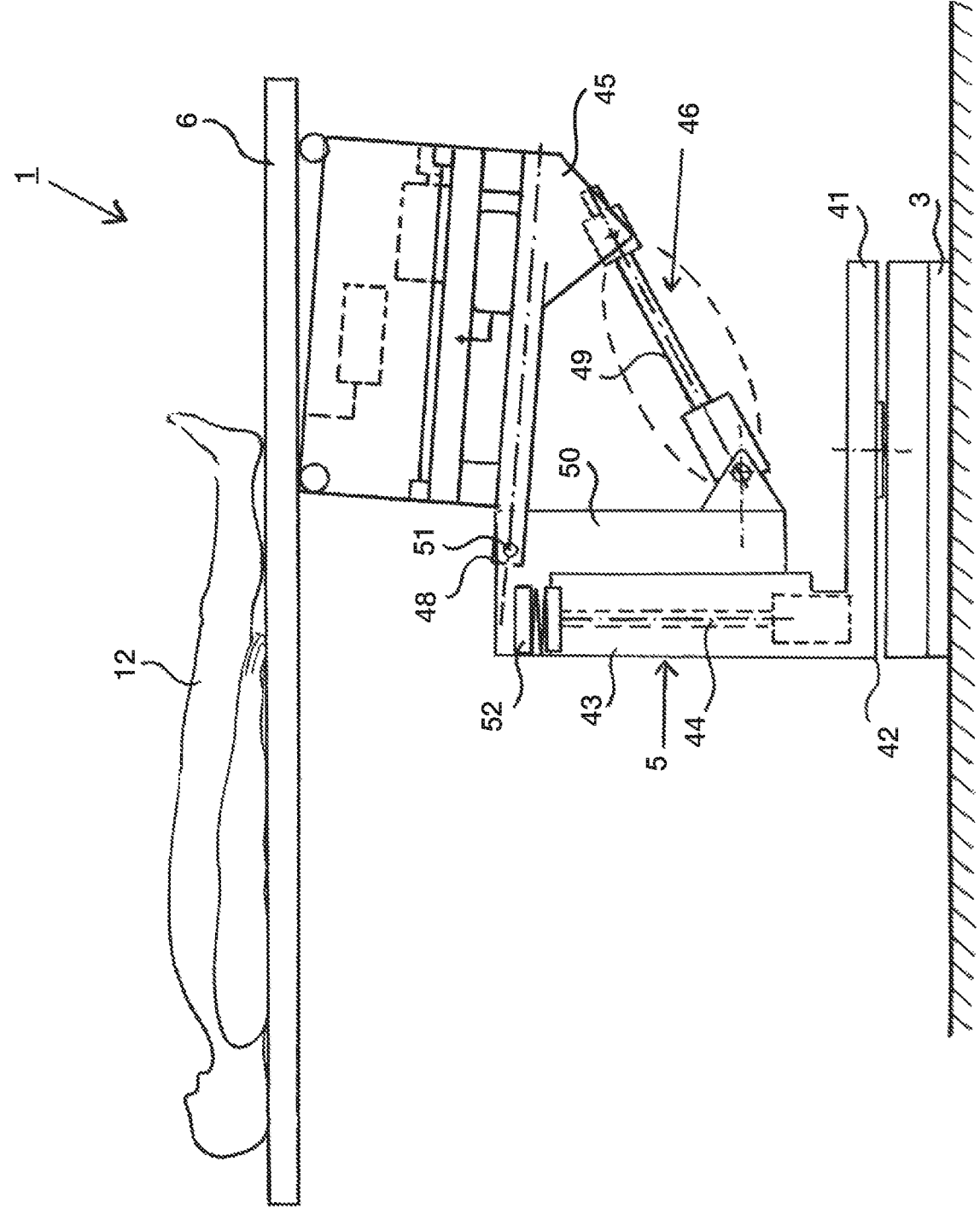

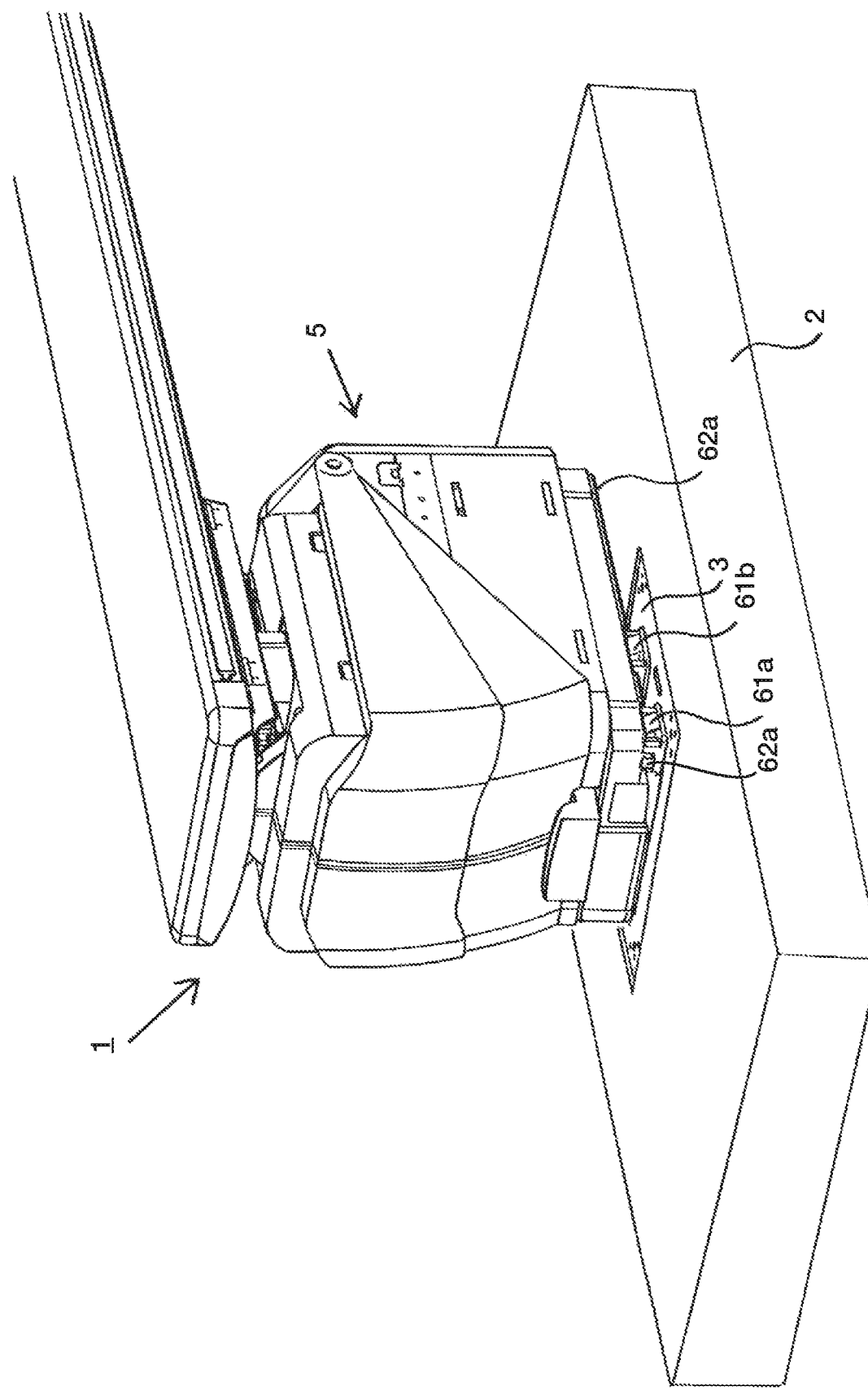

PATIENT SUPPORT SYSTEM AND LEVELLING SYSTEM FOR SUCH A PATIENT SUPPORT SYSTEM

CROSS-REFERENCE TO RELATED APPLICATIONS

This application represents the national stage entry of PCT International Application No. PCT/NL2015/050464 filed on Jun. 25, 2015, and is based upon and claims the benefit of priority from Netherlands Patent Application Nos. 2013070, 2013067, 2013071, 2013068, 2013069, all filed on Jun. 26, 2014. The disclosure of each priority application is incorporated herein by reference as if set forth in its entirety.

The current invention, from a first point of view, and according to a first aspect thereof, is related to a patient support system arranged to position and support a patient lying on the support system, for example at X-Ray Systems, especially Cardio/Vascular systems, comprising a frame that, in use, is mounted to a floor, an upright column with a table top support system and mounted to the frame and supporting a table top that is movable longitudinally with respect to the column and arranged to accommodate a person, at least one tilt actuator to move and/or maintain the table top in a set tilted position and a control device to control the at least one tilt actuator, the control device comprising an inclination measurement device, a data storage and a processing unit that in use compares data from the inclinometer with data from the data storage to command the tilt actuator to move/maintain the table top in the desired tilted position. The inclination measurement device can be an inclinometer, for example, or may be any arrangement to directly or indirectly measure the inclination of the table top.

Such a device is known, for example from U.S. Pat. No. 6,574,808 B1, disclosing an imaging table levelling system to level an imaging table with respect to true level. The levelling system has an inclinometer, a processor and actuators. The processor receives the table angle from the inclinometer and compares that data to a stored level constant. The processor then commands the actuators to move the imaging table until the table angle data matches the stored level constant.

A disadvantage of the known patient support system is that it is not accurate, since it does not take into account that the table top and the support system will bend or flex in response to, and dependent from, the load at the table top and the position of the table top with respect to the column. The table top and the support system need to be rigid, but the rigidity of the table top is limited because, amongst others, measures to make the table top more rigid may affect the quality of X-Ray images of a patient lying at the table top. The known patient support system is incapable to compensate for variables that will make the patient table and especially the table top bend in use.

The current invention aims to provide a patient support system that is able to bring and maintain the table top in a set tilted position more accurately than the known system. According to the current invention this is achieved in that the control device comprises a force sensor that in use determines a load supported by the table top and/or a position sensor that in use determines the longitudinal position of the table top with respect to a reference, wherein the control device in use calculates a set point for the at least one tilt actuator. This allows the control device to calculate the expected flexing of the patient table and especially the table top in dependence of, amongst others, the load at the table and/or the longitudinal position of the table top. The patient load can be determined by subtracting a force sensor measurement in an unloaded condition of the table top from an actual force sensor measurement (with a patient). The table top longitudinal position can be measured by the position sensor. The inclination will also depend on the rotational stiffness of the table top support, which is a constant value. The actual torque can be determined by multiplying the patient load times the table top longitudinal position compared to a reference point. The correction tilt angle can be calculated by dividing the actual torque by rotational stiffness. As well the reference point and the stiffness of the table top will be a constant for the patient support system. When the correction (angle) is measured, the control device can actuate the tilt actuator to move the table top to the desired tilted position, or to maintain in that position.

Compared to the prior art, an improved patient support system can be achieved by only applying one of the force sensor and the position sensor. Therefore claim 1 defines that the scope of protection includes a patient support system in which only one of both sensors is applied. However, the description only discloses a patient support system in which both sensors are incorporated, because of the mutually synergetic effect.

It is noted that US2012/0106701 A1 discloses an X-ray system wherein a motor assists manual lateral and longitudinal movement of a table top to decrease the necessary handling forces to move and/or position the X-ray system with respect to an object to be examined. To this end the tilt of the table top is measured and used as a parameter for the motor assist contribution. However, US2012/0106701 A1 fails to disclose at least one tilt actuator to move and/or maintain the table top in a set tilted position and a control device to control the at least one tilt actuator.

Advantageous embodiments of the invention will be explained below.

Preferably, the set tilted position of the table top is a substantial horizontal position. By maintaining a substantial horizontal position during use of the patient support system, the force required to move the table top with respect to the column is relatively low. It was an insight of the inventor that a reduction of the required forces to move or maintain the table top to or in a desired position is favorable to increase the accuracy of positioning the table top.

According to a preferred embodiment of the current invention a vertical support in the column supports a positioning table comprising motor arrangements that in use position the table top with respect to the column, which positioning table in turn supports the table top. The vertical support may comprise a vertical movement actuator to move the table top vertically with respect to the floor that supports the patient support system. An arrangement according to this preferred embodiment allows a rather direct movement of the table top with respect to the column.

It is preferred that the positioning table is attached to the vertical support at one end of the positioning table, and that the tilt actuator is supportingly connected to, or at least close to, the opposite end of the positioning table. In this way the positioning table is attached to the vertical support at a rather well defined position and will articulate about this position when the tilt actuator is driven to level the positioning table. This results in a rather stable support of the positioning table.

It is further preferred that the tilt actuator is a linear drive extending from the bottom part of the vertical support to the positioning table. According to this arrangement the tilt actuator extends in an angle in the range of −30 to +30 degrees, preferably −20 to +20 degrees with respect to the horizontal. This results in a triangle support for the positioning table so that a rather rigid construction can be achieved to support the positioning table, and thus also the table top.

The force sensor is preferably located between the top of the vertical support and the positioning table, especially at the position of the connection of the positioning table to the vertical support. As a result only the vertical load of the table top introduced in the vertical support is measured, which is the value that can be used in the control device.

According to the invention it is further preferred that the table top is made of a material that minimizes influence on X-Ray imaging of a patient lying on the table top. In prior art patient support systems used for X-Ray imaging of a patient rigidity of the table top is very important because the prior art systems are not able to compensate for flexing of the table top. Rigidity of the table top is also important for a patient support system according to the invention, however, since the patient support system according to the invention is able to compensate for flexing of the table top, rigidity of the table top may be less important than with prior art patient support systems. This the current inventions enables the use of materials for the table that have a minimum influence on an X-Ray image to be generated, even if this material results in a less rigid table top.

In an alternative preferred embodiment of the invention the force sensor is arranged for determining the load by motor measuring motor current of the vertical displacement. The longitudinal position of the table top can easily be determined from the value of the motor current.

According to a second aspect the current invention relates to a control device to control at least one tilt actuator of a medical device, especially a patient support system, comprising a table top to support a patient, the control device comprising an inclinometer, a data storage and a processing unit that in use compares data from the inclinometer with data from the data storage, to command the tilt actuator to move/maintain the table top in the desired angle of inclination, for example level, wherein the control device comprises a force sensor to determine a load supported by the table top and/or a position sensor to determine the longitudinal position of the table top with respect to a reference, wherein the control device in use calculates a set point for the at least one tilt actuator. Advantages of such a control device correspond to the advantages discussed above with respect to the first aspect of the current invention.

According to a third aspect the current invention relates to the use of a control device according to the second aspect of the current invention, especially in a patient table according to the first aspect of the current invention.

From a second point of view, the invention relates to patient support system and compact linear movement actuator for such a patient support system. According to a fourth aspect, the invention is related to a patient support system arranged to position and support a patient lying on the support system, for example at X-Ray Systems, especially Cardio/Vascular systems, comprising a frame that, in use, is mounted to a floor, an upright column mounted to the frame and supporting a substantially rectangular table top defining a plane and which is movable in said plane with respect to the column to accommodate a patient, and a controlling device with a motor and a gear for moving the table top to a desired position.

A known patient support system of this type comprises a table top that is floatable with respect to the column, to position the table top in an X-Ray imaging device. The table top can be moved by means of the motor and manually by medical personnel, and can be locked in position, for example when the table top with the patient is in the desired position to generate an image of the patient. Performance requirements of such patient support systems, like larger user strokes, safety brake systems and safer, faster and stronger movements constantly increase. Those increasing requirements result in the space in the column, available for housing the equipment becoming scarce, while increasing the column itself would cause ergonomic disadvantages. Besides the increasing requirements there is a constant need to reduce the footprint of the column.

The current invention according to this second point of view therefore aims to provide a patient support drive system of the above mentioned kind, in which less space is occupied by equipment, or the footprint of which can be reduced, with respect to a comparable known device. According to this second point of view of the current invention this is achieved in that the gear is a hollow axis angular gear. The use of an hollow axis angular gear makes it possible to develop a gear that is more compact and to place components, for example drive components, in the centre of the gear. Such an integration of functions reduces the required volume inside the column.

It is noted that this second point of view of the invention is described in the attached clauses a.1 to a.11, and can be used independently from the use of a force sensor and/or a position sensor.

In a preferred embodiment of the current invention according to the second point of view the motor has an output shaft that is at the same time an input shaft of an angular gear wheel of the angular gear. The output/input shaft is preferably embodied as a worm gear, which is an effective and reliable component to transfer a rotational movement of a motor to a gear wheel.

It is preferred that the angular gear input shaft directly engages and rotates the angular gear wheel when actuating the movement of the table top. This results in reliable and compact arrangement with only few components and thus contributes to the objective of the current invention.

In a preferred embodiment of the current invention an output pinion is at least partially enclosed in the hollow angular gear axis, which output pinion in use is actuated by the angular gear. Such an arrangement makes it possible to effectively use the space in the hollow angular gear axis. Further, this arrangement makes it possible to transfer the movement of the hollow angular gear axis to the pinion, as is discussed hereinafter.

In a preferred arrangement to convert the rotational movement of the output pinion into a linear movement of the table top the output pinion preferably engages a rack that is connected to the table top also. Such an arrangement is a reliable and compact arrangement contributing to the objective of the current invention.

It is preferred that a clutch is comprised in the patient support system according to the current invention, which clutch is switchable between an operational condition wherein the angular gear is in driving engagement with the pinion and a non-operational position in which the angular gear is not in driving engagement with the output pinion. The clutch thus allows the patient support system to be switched to a motor driven condition and a manually driven condition easily.

As will be understood by the skilled person, the driving engagement may be an indirect engagement, for example in an arrangement in which an angular gear and possibly other components are operationally arranged between the angular gear and the output pinion, if necessary.

Preferably the pinion is freely rotatable in the non-operational position of the gear. Thus, in the non-operational position a movement of the table top which is operationally connected with the pinion is not limited by the controlling device. This is important because it enables medical personnel to manually move the table top by engaging the table top without resistance resulting from the controlling device.

In a preferred embodiment the clutch is an electromechanical clutch. The mechanical components enable a reliable actuation of the movement of the table top which can be switched on and off electronically.

In a preferred embodiment of a patient support system according to the current invention a safety brake is provided to lock the controlling device when no movement of the table top is allowed. This enables the medical personnel to lock the movement of the table top once it is in the desired position for imaging a patient laying on the table top.

According to a fifth aspect the current invention is related to a controlling device for use in a medical device, especially in a patient support system, having a movable table top, and comprising a motor and a gear for moving the table top to a desired position, wherein the gear comprises a hollow axis angular gear. The advantages of a controlling device with the hollow axis angular gear corresponds to that of the fourth aspect of the current invention.

According to a sixth aspect the current invention is related to use of a controlling device, especially in a patient support system. Also the advantages of the sixth aspect of the current invention correspond to that of the fourth and fifth aspect of the current invention as discussed here above.

From a third point of view the invention relates to a patient support system and guiding device for a patient supporting system. The current invention, according to a seventh aspect thereof, relates to a patient support system arranged to position and support a patient lying on the support system, for example an X-Ray system, especially Cardio/vascular systems, comprising a frame that, in use, is mounted to a floor, an upright column mounted to the frame and supporting a substantially rectangular table top defining a plane and which is movable longitudinally with respect to the column to accommodate a patient, the patient support system comprising a guiding device developed to guide the column from a first position with respect to the floor to a second position with respect to the floor.

A known patient support system of this type has a guide system comprising two wheels; both having a substantially vertical rotation axis; one of which wheels is fixed in position with respect to the floor, the other fixed in position with respect to a column base of the column, which wheels are rotatable in the same plane and around which a belt is wrapped. The column and the frame are supported and mutually connected through mutually articulating arms. When one of the wheels is driven in rotation, the belt will move together with said wheel and will thus rotate the other wheel. As a result, the patient support system will be guided from a first position to a second position, the second wheel describing a curved path around the first wheel.

A disadvantage of the known device is that the guide with the two wheels requires relatively much space. To assure a safe working environment without elements visibly projecting from the floor, the column or a cover extending outside a footprint of the rest of the column should cover the wheel that is fixed to the floor, in all positions of the column. That requires quite some cross section surface for the column. Besides that, since the column describes a curved path, space is required to make such a curved path possible. The curved path and the cover also affect the cleanability of a room that houses the known patient support system.

An objective of this aspect of the current invention is to provide a patient support system of the kind described above, which requires less space for the column and the path thereof. The smaller the column, the more ergonomic the working environment for the medical staff. The objective is achieved by this aspect of the current invention in that in use the guiding device is arranged to guide the column in a rectilinear path between the first and the second position. As a result, no space is required within the column to allow the column to move sideward. This allows the column to be designed with a smaller width dimension. Also as a result, no space is required within the column to accommodate a wheel which is present in the known device and that is fixed to the floor in both positions, so at opposite sides of the second wheel fixed to the column. Further, a linear bearing can be developed more rigid than the known guide.

It is noted that this third point of view of the invention is described in the attached clauses b.1 to b.16, and can be used independently from the use of a force sensor and/or a position sensor.

While the guiding device is defined to be developed to guide the column with respect to the floor, the guiding device could be incorporated at the top of the column to extend the table top with respect to the column, for example in combination with a conventional table top floating system. The effect is comparable, a larger extension of the table top. A drawback could be that the moment of the table top with respect to the attachment to the column increases, as a result of which the table top could bend to a larger extend. In this alternative case, the user could consider to accept the higher degree of flexing. But this alternative can be considered as an equivalent of the arrangement according to this third point of view described above (in particular, equivalent to the arrangement according to clause b.1). It is even possible to integrate a guiding system according to the invention in the top and another one in the bottom of the column. As a result the column can be moved along the floor and the table top can be moved with respect to the column.

EP 2 226 010 A1 discloses a patient table supported by wheels to allow the patient table to be driven over a floor, to position the patient table with respect to an X-ray device. The drivable patient table has a bottom frame that extends very close to the floor, and over a distance that corresponds to a projection of the table top. The bottom frame houses a column and a guiding to move the column with the table top in a longitudinal direction of the table top. The table top itself can be moved transversely, but explicitly not longitudinally, to prevent that the table top must be strengthened, which could negatively affect the quality of X-ray images of a person lying at the patient table.

In a preferred embodiment of the current invention the guiding device comprises at least one first, relatively long guiding element connected to the column and at least one second, relatively short guiding element mounted to the floor, the first and second guiding elements being in mutually guiding engagement, wherein the terms relatively long and relatively short are used to indicate that the relatively long guiding element is longer than the relatively short guiding element. Such an arrangement has the beneficial effect compared to arrangements wherein for example a rail is mounted to the floor, that as well in the first position as in the second position no guiding element extends outside the column, or at least a footprint of the column. Such protrusions would cause a serious risk for personnel working in the room wherein the patient support system is installed. People may stumble on such protrusions, when present.

In such an arrangement the patient support system preferably comprises at least two second, relatively short guiding elements that are spaced apart and aligned in the guiding direction and both being in guiding engagement with the at least one first guiding element. The relatively short guiding elements, which may be interconnected, provide a stable basis for a rigid guiding of the column when moving with respect to the floor. The length of the relatively long guiding element ensures that the relatively long guiding element can be in engagement with the second guiding element(s) over a relatively long distance. This also contributes to a rigid arrangement for the column when moving with respect to the floor.

The at least two second guide elements preferably are mutually connected by means of a mounting element. The mounting element can contribute to a better alignment of the two second guide elements with respect to each other, resulting in a more rigid and/or reliable arrangement.

A very stable and rigid arrangement for moving and guiding the column with respect to the floor can be achieved if the guiding device comprises at least two guiding mechanisms arranged in parallel, i.e. both extending in the direction of movement of the column.

When the at least two guiding mechanisms are mutually connected by means of a mounting plate, a very rigid guiding arrangement can be provided.

In a preferred embodiment of an arrangement in which the at least one first, relatively long guiding element is connected to the column and at least one second, relatively short guiding element is mounted to the floor, the at least one first guiding element preferably is a guide rail that extends substantially over the full length at the bottom of the column. As such, the column can be moved to a relatively large extend over a distance corresponding to the longitudinal dimension of the column, especially the guide rail, minus the opposing end(s) of the second guiding element(s), still preventing that the second guiding element(s) extend to beyond the footprint of the column in any position of the column with respect to the floor.

In a preferred embodiment of the current invention the at least one second guiding element is a guiding shoe.

The at least one second guide element, or, when the patient support system comprises at least two second, relatively short guiding elements that are spaced apart and aligned in the guiding direction and both being in guiding engagement with the at least one guiding element, the mutually aligned second guiding elements engaging the same first guiding element, extend(s) over a total distance of no more than ⅔, preferably no more than ½ and more preferably no more than ⅓ of the length of the column in the guiding direction. The smaller the total distance over which the second guiding element(s) extend, the larger the stroke that the column can make, given the length of the first guiding element, still preventing the first guiding element to protrude to outside the footprint of the column.

In a preferred embodiment the column comprises at least one locking mechanism to lock the column in each of the first and second positions. The first and second positions are operational imaging positions in which the table top needs to be fixed as play-free as possible to be able to make an image of a patient lying on the patient supporting device. If the patient supporting device comprises more positions in which an image of a patient can be made, the at least one locking mechanism preferably is developed to lock the column in such position(s).

In a preferred embodiment of the patient supporting device according to the current invention, the patient supporting device comprises a position sensor that, in use, detects the position of the column with respect to the floor. The position sensor can provide a feedback relating to the position of the column to a control device of the patient supporting device.

When the at least one second guide element is mounted at least partially sunk in the floor, a mounting element to which the at least one second guiding element is attached can be arranged sunk in the floor. An advantage of such an arrangement is that the minimal horizontal position of the table top with relation to the floor is decreased, which can be beneficial in terms of ergonomic performance of the table for medical personnel and for patients when getting on and off the table top.

In a preferred embodiment of the current invention the patient supporting device comprises arrangements to move the table top transversely or vertically with respect to the column. Together with the longitudinal movability of the table top, the table top can be positioned in a three-dimensional space.

According to an eight aspect the current invention relates to a guiding device developed to guide a column of a patient table from a first position with respect to a floor to which the patient table is attached to a second position with respect to the floor. Such a device is known and discussed in one of the previous paragraphs of this document, together with the disadvantages of such a device. According to the eight aspect, the current invention aims to provide a guiding device as discussed in the introduction of this paragraph, which requires less space for a column and a path thereof, of a patient table in which the guiding device is comprised. This object is achieved in that, in use, the guiding device is arranged to guide the column in a rectangular path between the first and the second position. Of course, the preferred embodiment of the guiding device of the patient table discussed herein and with respect to the seventh aspect of the invention can be applied to the guiding system of this eight aspect of the invention.

According to a ninth aspect, the current invention relates to the use of a guiding device according to the eight aspect of the current invention, preferably in a patient support system according to the seventh aspect of the current invention. The advantages of the use of such a device and/or system are discussed here above.

From a fourth point of view, the invention relates to a patient supporting system comprising a holding brake, and a holding brake. The current invention, according to a tenth aspect thereof, relates to a medical device attached to a static frame and comprising a movable part and a holding brake device to hold the movable part in a set position.

Medical devices according to the above mentioned kind are known. A known patient support system for patient positioning at X-ray systems, especially a cardio/Vascular system for example, has a frame that is mounted to the floor. Mounted to the frame is an upright column that is rotatable around a longitudinal axis thereof. On top of the column is a rectangular table top, for in use supporting a patient lying at the table top. The table top is mounted to the column at or near an end of the table top. The table top is arranged to rotate together with the column. A holding brake is mounted to the frame, to, in an activated condition thereof, prevent rotation of the column and the table top in set position. The known holding brake, which may also be considered as a locking system, comprises a toothed ring that rotates with the column and a rack having teeth that cooperate with the teeth of the toothed ring. In the inactivated condition of the holding brake, the toothed ring is freely movable to allow rotation of the column with the table top and that engages the rack. In the activated condition of the holding brake the rack is locked, with the result that the teeth of the rack, and thus also the teeth of the toothed ring are fixed in position to prevent rotation of the column and the table top. A disadvantage of the known device, however, is that the holding brake is vulnerable for play and hysteresis in the movement direction when the brake is applied, especially noticeable when there is a large leverage between the objects that are being braked. To increase the holding power of the known holding brake a stronger and thus more voluminous actuation device or even an additional brake is required.

This aspect of the current invention aims to provide a medical device of the type described above with a holding brake device which is less vulnerable for play/hysteresis than the known device and/or that can be varied in maximum holding power without substantially affecting the space required for the holding brake device. According to the invention this is achieved with a patient support system that comprises at least two first, static brake plates extending from the at least one static component, parallel to the reference plane, and, seen perpendicularly to the reference plane, side by side, and at least two second movable brake plates extending from the at least one movable component, parallel to the reference plane, and at least in the activated condition of the holding brake device partly overlapping the first brake plates, wherein the at least two first and at least two second brake plates, at least in the activated position of the holding brake device, are arranged alternatingly, and comprising a pressure assembly that applies a normal force to the brake plates to activate the brake device and releases said normal force to inactivate the brake device. In particular this is achieved with a patient support system as described by clause c.1.

In this document, and in particular in line with the fourth point of view of the invention, the activated condition of the holding brake device is the condition in which the holding brake device locks the column against moving with respect to the frame. Thus, in a so-called "normally on" arrangement, the holding brake device is switched "off" in the activated condition.

Known holding brakes of medical devices, such as patient support systems, incorporate at least one guidance mechanism to let friction surfaces of the holding brake touch each other in a parallel way in order to get good surface to surface contact. Such guidance mechanisms cause the play/hysteresis in the movement direction when the brake is applied.

In a holding brake device according to the fourth point of view of the invention no such guidance system is present. Instead, the first and second brake plates can be spaced apart to minimize resistance when rotating the table top in the inactivated condition of the holding brake device. However, it is not even required to space the brake plates apart. The distal ends of the brake overlap and of course the overlapping brake plates create material distance between two neighbouring brake plates of the same kind, at the location of overlap. This may be achieved by bending neighbouring plates away from each other. Even if some adjacent brake plates would be in contact in the inactivated condition of the holding brake device, they are not used as a guidance mechanism and the contact causes only minimal resistance.

It is noted that this fourth point of view of the invention is described in the attached clauses c.1 to c.16, and can be used independently from the use of a force sensor and/or a position sensor.

When, as in a preferred embodiment the brake surfaces are made of thin sheet metal, the brake surfaces can be designed 'not stiff' perpendicularly to the movement direction. Therefore they easily form good friction surface to friction surface contact, while being fixed (which implies there is no play). In the movement direction they are stiff, so when trying to push through the brake, there is really little deflection. This gives the feel that the object being braked is standing still, even with a big force applied.

The first and second brake plates can be designed to provide opposing friction surfaces and to deflect easily to form good friction surface to friction surface contact if the pressure assembly applies a normal force to the brake plates. The holding force of the holding brake device according to the invention is a function of the normal force exerted to the brake plates, the coefficient of friction of the friction surfaces and the number of friction surfaces between the brake plates. Because the relatively large number of brake plates, and thus friction surfaces, only a relatively low normal force is required to result in a relatively high braking power. The dimensions of the mutually contacting surface areas and the number of first and second brake plates can be easily increased to increase the holding power, without substantially affecting the rotatability of the table top in the inactivated condition of the holding brake device. Because the brake plates are relatively thin, increasing the number of brake plates requires only very little additional space. Thus, the objective of the current invention is achieved. While the arrangement of a holding brake device according to the invention is able to generate a relatively high holding force, it is not excluded that additional holding brake devices could be added to further increase the holding power, or as an (additional) safety brake.

US 2005/0068137 A1 discloses a holding brake arrangement with a movable sheet as part of a medical device and enables moving and positioning of the device. The sheet is sandwiched between a fixated sheet and an electromagnet. When the electromagnet is switched on, an electromagnetic holding force is generated and the electromagnet clamps the movable sheet against the fixation sheet. There exist two friction surfaces, one between the electromagnet and the movable sheet and one between the movable sheet and the fixation sheet. If the electromagnet is switched off, and the electromagnet is no longer in contact with the movable sheet, and thus the movable sheet can move again.

In a preferred embodiment according to the current invention a brake plate is preferably made of metal. In general metal plates especially if the surface is a little buffed comprise a friction coefficient which is suitable for use in a holding brake device. A relatively small normal force can result in good holding characteristics. However, other suitable materials can be used for the holding brake plates.

The holding capacity of a second brake plate are preferably made of a dissimilar material, preferably two different kinds of metal. However, it would be possible to the same material for the first brake plates than for the second brake plates.

The holding capacity of a holding brake device according to the current invention is proportional to the number of friction surfaces available in the device. Therefore, the holding brake device preferably comprises at least three, more preferably at least four first brake plates. In other words, the holding brake device preferably has at least three friction surface pairs. With two first brake plates and two second brake plates there are already 3 friction surface pairs.

For the same reason the holding brake device of the patient support system according to the current invention preferably comprises at least three, more preferably at least four second brake plates. The first and second brake plates preferably are arranged alternatingly, wherein the number of second brake plates is preferably equal to, or one more or less than, the number of first brake plates. It is possible to arrange the first or second brake plates without an intermediate second or first brake plate respectively. In that case two opposing friction surfaces of the brake plates of the same kind will not influence the holding power of the holding brake device.

In a preferred embodiment of a patient support system according to the current invention a surface of an outer brake plate facing away from the other brake plates is covered with a resilient material. This resilient material help to prevent and to level out peak contact stress at the friction surfaces.

The resilient layer is preferably made of rubber.

To assure a good holding capacity in a relatively compact brake device, the thickness of the brake plates is in the range of 0.02-4.0 mm, preferably in the range of 0.05-2.0 mm and even more preferably in the range of 0.75-1.5 mm. The brake plates should not be vulnerable to damage. On the other hand, the thicker the brake plates, the more difficult the brake plates will deflect, for example when a normal force is applied to the brake plates, or if the normal force is released activate and inactivate respectively the holding brake device.

In a preferred embodiment according to the current invention two adjacent first brake plates and/or two adjacent second brake plates are spaced apart, or at least overlapping parts of the brake plates are spaced apart.

A spacing between brake plates is preferably provided by a holding brake device wherein a spacer is arranged between two adjacent first brake plates and/or between two adjacent second brake plates. The spacer helps to create room for a brake plate of the other type to be present between the adjacent brake plates. As a result the brake plates can extend straight, thus without deflecting, for example from a mounting block in which the brake plates are mounted. Spacers can keep the first and second brake plates relatively parallel to each other, so the force to make good friction surface to friction surface contact is even less than without them. Besides that, spacers can be made of inexpensive sheet metal, so cost price impact of adding spacers is little. The spacer has preferably the same thickness as the brake plates.

In a preferred embodiment of the current invention the pressure assembly comprises an electromagnetic actuator to activate and/or inactivate the holding brake device. The electromagnetic actuator can be used to activate the holding brake device in the powered condition of the electromagnetic switch in a normally open system. However, for safety reasons it is preferred to inactivate the holding brake device when the electromagnetic actuator is powered in a normally closed arrangement.

Additionally or alternatively the pressure assembly may comprise a mechanical spring, such as a helical pressure spring in a normally closed arrangement of the holding brake device, for example. The helical pressure spring will apply a normal force to the brake plates. If an electromagnetic switch is powered, the electromagnetic switch will release the normal force of the helical pressure spring to inactivate the holding brake device.

In a preferred embodiment of the holding brake device according to the current invention the first, static brake plates are ring-shaped and are arranged such that a rotation axis of the movable part of the column of the patient support system extends perpendicularly through the centre or the ring-shaped brake plates. In such an arrangement the second movable brake plates extend to in between the first static brake plates. In the activated condition of the brake the normal force prevents the medical device to rotate about the rotation axis. In the inactivated condition of the holding brake device the patient support system is allowed to rotate. However, an arrangement wherein, instead of the first, static brake plates, the movable brake plates are ring-shaped can be considered as well.

Alternatively, or additionally, the movable part of the patient support system is arranged to be translatable, and the brake plates are arranged rectangular. In such an arrangement the patient support device is able to translate in an inactivated condition of the holding brake device.

Alternatively or additionally the path of movement of the movable part of the medical device is complex, and static first brake plates extend at least substantially correspondingly to the path of movement of the movable brake plates, wherein complex is to be interpreted as any other arrangement than a linear path that can be generated in case of a linear drive, or a circular path that can be generated by a rotational drive. In that case, if the patient support device can be moved along the complex path. The movable brake plates will stay between the static brake plates.

According to a eleventh aspect the current invention relates to a holding brake device for use in a medical device, especially in a patient support system, developed to position and support a patient lying on the support system comprising a frame that is, in use, mounted to a floor and an upright column that is mounted to the frame and that is movable with respect to the frame. In a preferred embodiment the column is at least rotatable with respect to the frame and the holding brake is arranged to, in use, hold the frame from moving, for example. The holding brake device comprises at least one static component and at least one movable component, movable with respect to the at least one static component in a reference plane, the holding brake device being arranged to prevent the at least one movable component to move parallel to the reference plane in an activated condition of the holding brake device and to allow the at least one movable component to move parallel to said reference plane in an inactivated condition of the holding brake device, at least two static brake plates extending from the at least one static component and parallel to the reference plane and, seen perpendicularly to the reference plane, side by side and apart, and at least two second movable brake plates extending from the at least one movable component and parallel to the reference plane, and at least in the activated condition of the holding brake device partly overlapping the first brake plates, wherein the first and second brake plates are arranged alternatingly, and a pressure assembly that applies a normal force to the brake plates to activate the brake device and releases said normal force to inactivate the brake device has advantages that correspond to the advantages discussed above with respect to the tenth aspect of the current invention.

According to a twelfth aspect the current invention is related to the use of a holding brake device according to the eleventh aspect of the current invention in a medical device, for example a patient support system according to the tenth aspect of the current invention. Again, the advantages of the twelfth aspect of the current invention correspond to that of the tenth and eleventh aspect of the current invention.

From a fifth point of view, the invention relates to a patient support system and clutch for a compact linear movement actuator in a patient support system. The current invention, according to a thirteenth aspect thereof, is related to a patient support system arranged to position and support a patient lying on the support system, for example at X-Ray systems especially Cardio/Vascular systems, comprising a frame that is, in use, mounted to a floor, an upright column mounted to the frame and supporting a substantially rectangular table top defining a plane and which is movable in said plane with respect to the column to accommodate and position a patient, and a controlling device with a motor and a gear for moving the table top to a desired position and a clutch for activating and deactivating the gear assembly.

A known patient support system comprises a table with a table top that is floatable with respect to the column, to position the table top in an X-Ray imaging device. The table top can be moved by means of the motor and manually by medical personnel, and can be locked in position, for example when the table top with the patient is in the desired position to generate an image of the patient. Performance requirements of such patient support systems, like larger user strokes, safety brake systems and safer, faster and stronger movements constantly increase. Those increasing requirements not only result in the space in the column, available for housing the equipment becoming scarce, but also in an increasing number of components. An increasing number of components, however, compromises the safety of the patient support system. In other words, more functionality in a smaller available column volume makes that a solution with all the functions stacked would not fit in the column.

Therefore, it is an objective of the current invention according to the fifth point of view to provide a patient support system enabling a reduction of the number of components with respect to a comparable patient support system with at least the same functionality, and/or that can be designed more compact. This objective is achieved by the current invention in that the controlling device comprises an electromechanical brake as the clutch. An electromechanical brake in principle requires two main components, a magnet and a friction part and can thus be designed relatively compact, while a conventional clutch requires at least an actuation part and two rotating friction parts. Thus, the objective of the current invention is achieved with the features as described in the characterising part of clause d.1.

It is noted that this fifth point of view of the invention is described in the attached clauses d.1 to d.11, and can be used independently from the use of a force sensor and/or a position sensor.

In a preferred embodiment of the current invention the electromechanical brake is integrated in the gear assembly. Integration in the gear assembly enables to achieve a rather compact arrangement of the controlling device.

It is preferred that the electromechanical brake comprises a coiled magnet and a first friction element that is movable with respect to a second friction element of a component to be switched between a locked condition an a released condition, between an operational position wherein the first and second friction elements are mutually in engagement and a non operational position wherein the first and second friction surfaces are disengaged. In such an arrangement the second friction element can be integrated in an actuation part of the gear assembly, also enabling a relatively compact embodiment of the controlling device.

It is preferred in that aspect, that the clutch is arranged to be in the locked position when the clutch is not powered. As a result the table top of the patient support system will not be able to move (float) if the electromechanical brake is not powered. Thus, in a situation where the power supply is disturbed the table top is in a fixed condition, or at least there will be no freedom of movement in the direction in which the current actuator is intended to move the table top. This increases the safety of the patient support system. However, alternatively it could be possible to develop a patient support system according to the current invention wherein the clutch is in the locked position when the clutch is powered.

In a preferred embodiment according to the current invention the second friction element is comprised in, or fixed to, an actuation part of the gear assembly. This also enables a rather compact design of the controlling system and a reduction of the number of parts necessary for the patient support system.

It is preferred if the electromechanical brake is arranged in parallel with a hollow axis angular gear, and if the electromechanical brake also comprises a hollow axis, which is at least substantially aligned with the hollow axis of the gear wheel. When both hollow spaces are aligned it is possible to mount an output pinion of the gear assembly through the space within the electromechanical brake and the hollow axis angular gear. This also enables a very compact controlling device and a reduction of the number of parts of the controlling device since the transmission of the movement of the actuating parts to the part to be actuated can be embodied in a simple way.

In such a device it is preferred that a rotary electrical feed through is provided, preferably embodied as a slip ring, to power the electromechanical brake.

The gear assembly is preferably developed to linearly move the table top in the rectangular plane of the table top, especially in the longitudinal direction of the rectangular plane. The stroke of the table top in the longitudinal direction may be rather long and forces exerted at the electromechanical brake as a clutch can be quite large. A controlling device in a patient support system must be reliable at all times. Therefore a patient support system with a controlling device according to the current invention can be developed reliable, compact and with a relatively small number of components.

According to a fourteenth aspect the current invention relates to a controlling device for use in a medical device, especially a patient support system according to the thirteenth aspect of the invention, having a table top the controlling device comprising a motor and a gear assembly for moving the table top to a desired position, a clutch for activating and deactivating a gear assembly to actuate movement of the table top and a brake to lock the table top in the desired position, characterised in that the controlling device comprises an electromechanical brake as the clutch.

The advantages of such a controlling device correspond to the advantages discussed above with respect to the twelfth aspect of the current invention.

According to a fifteenth aspect the current invention relates to the use of a controlling system according to the fourteenth aspect of the current invention, preferably in a patient support system according to the thirteenth aspect of the current invention. Again the advantages of the use of such a controlling system correspond to the advantages discussed herein above.

The different aspects of the invention will now be described in more detail with reference to the figures that show a preferred embodiment of a patient support table according to the invention and wherein:

FIG. 5b is a schematic side view of the levelling device of FIG. 5a supporting a patient;

FIG. 6b is a perspective view of the guiding system of FIG. 6a with the column in an opposite location;

In the different figures the same parts are referred to with the same reference numbers to overcome an unnecessary repetition of introduction of reference numbers. The orientation of components of the patent table must not always be taken absolutely. The orientation of some parts may differ from the unloaded condition in the loaded condition (compare FIGS. 5a and 5b, for example). The term level, however, is to be interpreted as horizontal as possible under the given circumstances.

Figure 1:
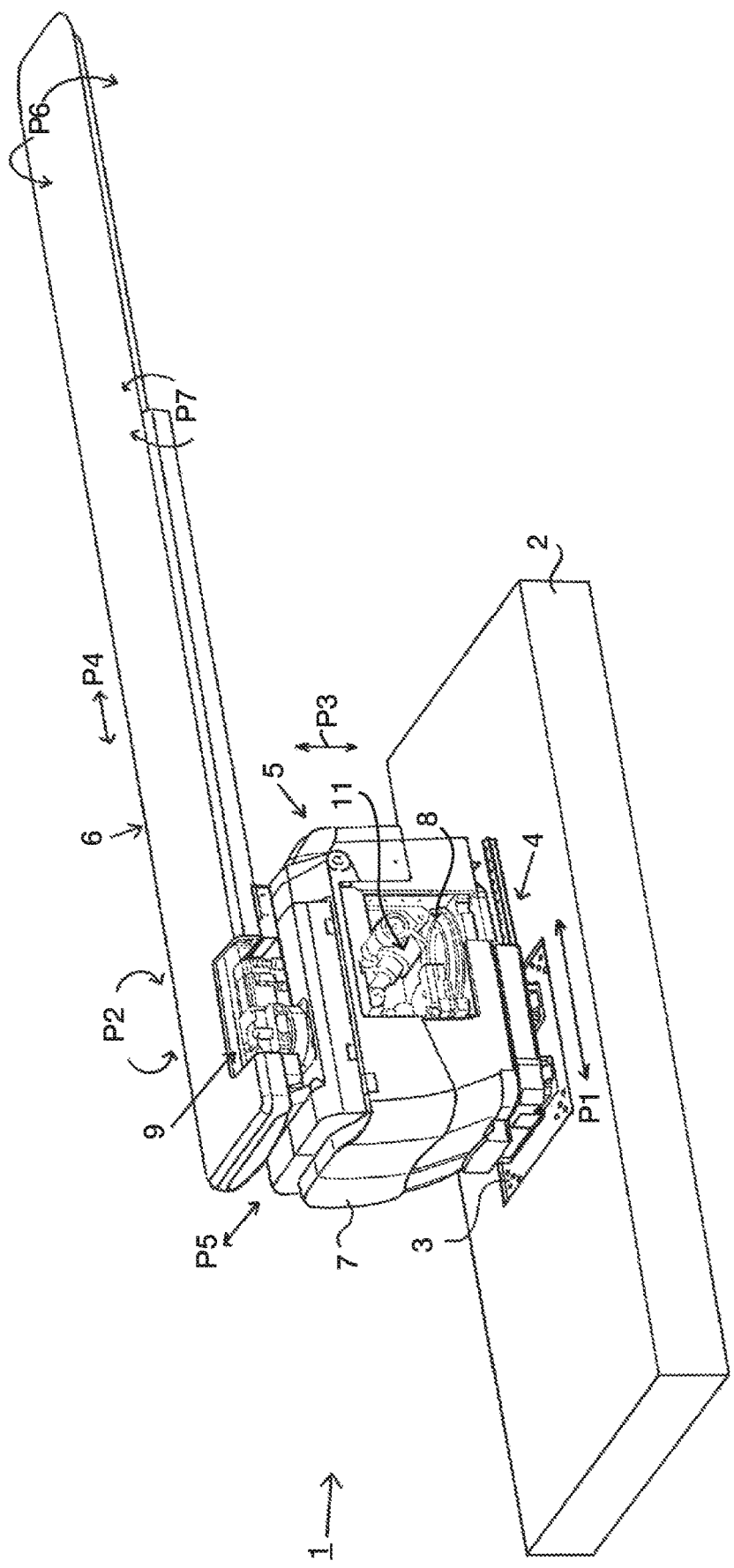
FIG. 1 is a perspective view of a patient table according to the invention.

Now referring to FIG. 1 a patient table 1 is shown in a perspective view as an embodiment of a patient support system according to the current invention. Patient table 1 is arranged to support a patient of which an X-Ray image must be generated, especially to manoeuvre and maintain the patient in a desired location with respect to an X-Ray imaging device (not shown). The patient table 1 is mounted to a floor 2 of a medical room to which in use is fixed, and wherein is preferably sunk, mounting plate 3 as part of a frame through which the patient table 1 is installed in the medical room. A guiding system 4, which will be discussed more in detail herein later, is present between the mounting plate 3 and a column 5 that carries a table top 6. The column 5 has a housing 7 enclosing many components, amongst which a control system to control movements of the patient table 1 to, in use, move the table top 6 and a patient lying thereon to, and maintain it in, a desired position. A ring guide system 8 is enclosed in the bottom of the housing 7 of the column 5. The control system comprises a levelling device (not shown in FIG. 1) that will be discussed later herein to maintain the table top 6 level, or in another defined angle of inclination, in the loaded condition of the table top 6. A compact linear drive 9 on a positioning table 45 on top of column 5 serves a longitudinal movement of the table top 6 with respect to the column 5.

The patient table 1 is able to make many movements to be able to move and maintain the table top 6 with a patient in a desired position with respect to an X-Ray imaging device. The column 5 is able to translate, supported by the guiding system 4, in a direction indicated by P1 with respect to a floor of a medical room to which the mounting plate 3 is attached. The column 5 is also able to rotate about a generally vertically extending rotation axis, driven and supported by a ring guide system 8 and in a direction indicated by arrow P2. The column 5 is also able to move generally vertically in a direction indicated by arrow P3, for which movement a cylinder (not shown in FIG. 1) is present in a levelling device to be discussed. The table top 6 is able to move longitudinally with respect to the column 5 in a direction indicated by arrow P4, driven by the compact linear drive 9 that is discussed later herein. The table top 6 is also able to translate transversely with respect to the column 5 in a direction indicated by arrow P5, to rotate about its longitudinal axis in a direction indicated by arrow P6 and to tilt with respect to the horizontal in a direction indicated by arrow P7. The control of the movements in the directions P5-P7 happens in a way that is known from patient tables that are commercially available and will not be discussed in detail herein.

Figure 2:
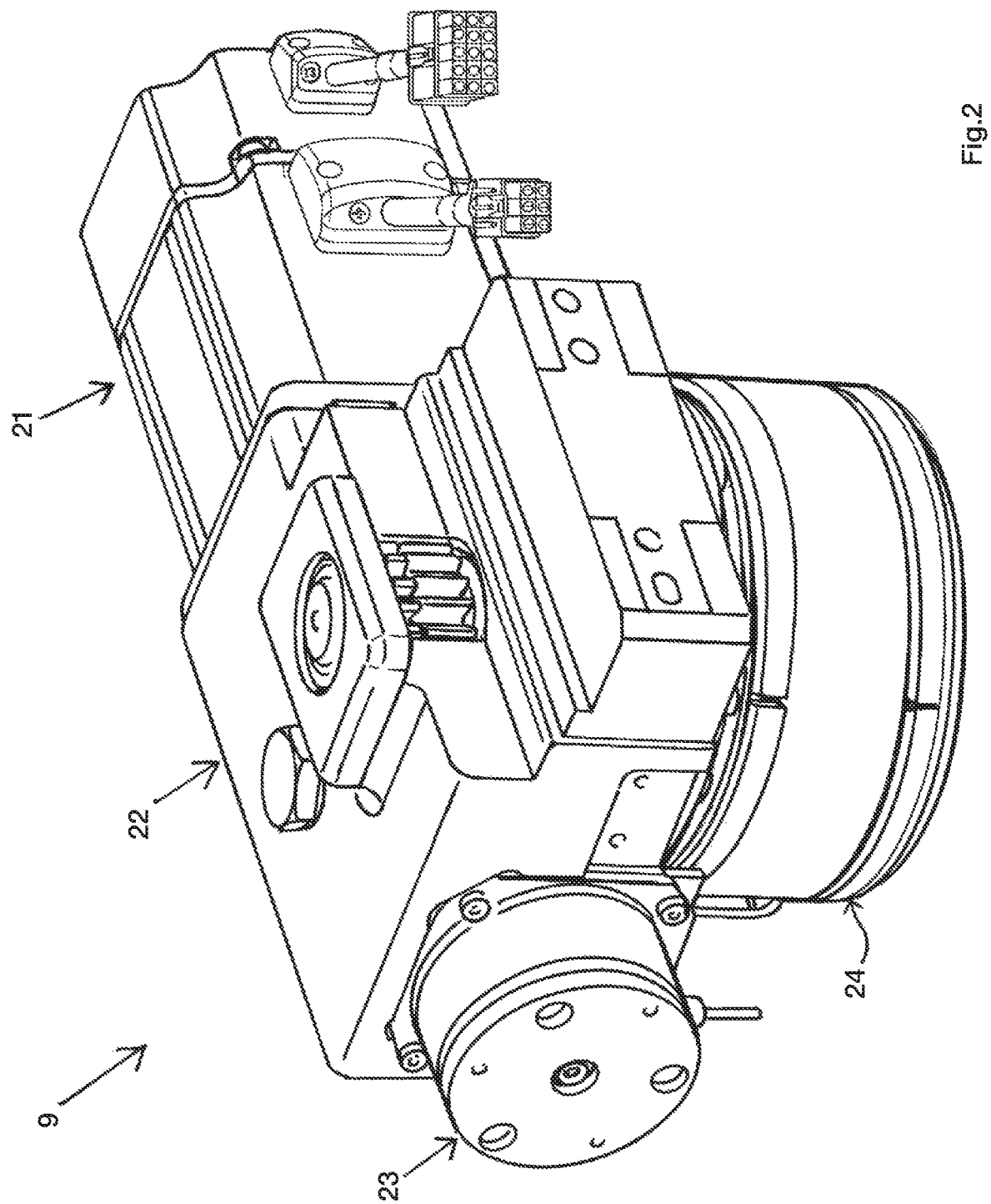
FIG. 2 is a perspective view of a compact linear drive for a table top of the patient support table of FIG. 1.

FIG. 2 shows a perspective view of the compact linear drive 9 for the table top 6 of the patient support table 1. The compact linear drive 9 comprises a motor 21, a gear box 22, a safety brake 23 and an electromechanical brake 24 as a clutch.

Figure 3:
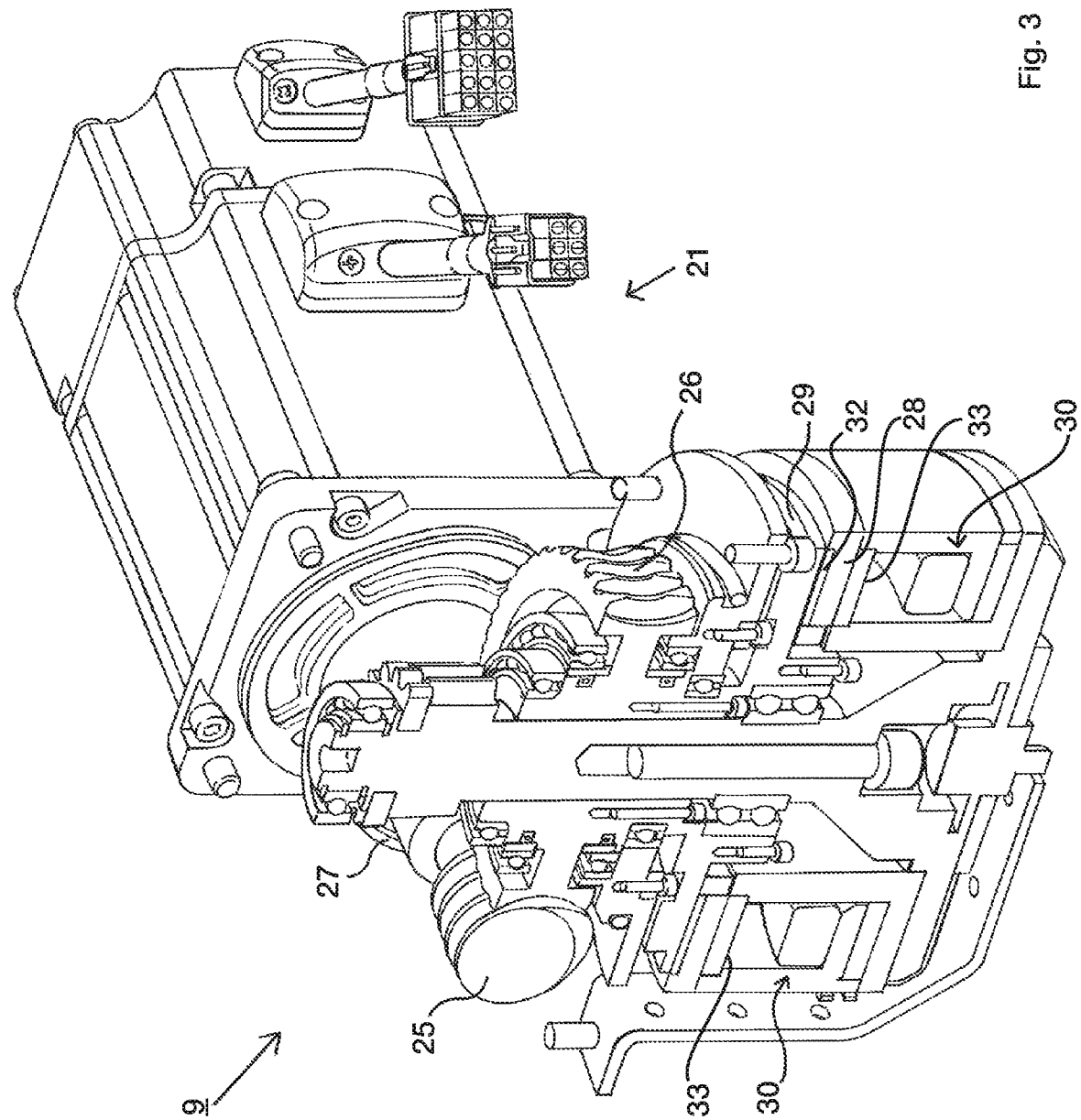
FIG. 3 is a perspective view, partly in cross section, of the compact linear drive of FIG. 3 with the housing removed.

FIG. 3 shows the compact linear drive 9 in more detail in a perspective view, partly in cross section and with the housing of the gear box 22 removed. The motor 21, a conventional electromotor, has an output shaft 25 embodied as a worm 25. The worm 25 is in engagement with a worm gearwheel 26 which, in an operational condition, is able to rotate with a pinion shaft 27. The worm gearwheel 26 has a hollow axis, through which the pinion shaft 27 extends. As a result, a relatively compact drive arrangement is achieved. A clutch 24 embodied as an electromechanical brake 24 is operationally arranged between the worm gearwheel 26 and the pinion shaft 27. In use, the motor 21 of the compact linear drive 9 rotates the worm 26, which in turn rotates the worm gearwheel 26. In the mutually coupled condition of the worm 25, the worm gearwheel 26 and the pinion shaft 27, the worm gearwheel 26, in turn, rotates the pinion shaft 27.

The clutch 24 is embodied as an electromechanical brake. An adapter flange 29 is in connection and rotates together with the worm gearwheel 26. The lower surface of the adapter flange 29 faces to an upper surface of a friction disk 28. A leaf spring 32 is provided between the lower surface of the adapter flange 29 and the upper surface of the friction disk 28 and is pulled downward in the non-powered condition of the electromechanical brake 24. Located below the friction disk 28 is a magnet arrangement 30 comprising a permanent magnet that attracts friction disk 28. The magnet arrangement 30 further comprises an electromagnet that, in a powered condition of the electromagnet, compensates for the attractive force of the permanent magnet and the force of the leaf spring 32.

Both the lower surface of the friction disk 28 and the upper surface 33 of the magnet arrangement 30 are provided with a friction surface. In the non-powered condition of the electromechanical brake 24, the friction disk 28 and the upper surface 33 of the magnet arrangement 30 are in mutual engagement. In this condition, the pinion shaft 27 will rotate if the worm gearwheel 26 is rotated. In the powered condition of the electro mechanical brake 24 as a clutch, a gap is present between the friction disk 28 and the upper surface 33 of the magnet arrangement 30 because the attractive force of the permanent magnet is compensated by the electromagnet. Now the friction disk 28 and the upper surface 33 of the magnet arrangement are disengaged. In this condition, the pinion shaft 27 is freely rotatable and will not rotate if the worm gearwheel 26 is rotated. An arrangement in which the powered and non powered conditions are interchanged, however, is also possible.

The magnet arrangement 30, like the worm gearwheel 26 has a hollow axis that is aligned with the hollow axis of the worm gearwheel 26. This enables the pinion shaft 27 to extend through the hollow axes of both the worm gearwheel 26 and the magnet arrangement 30. As can be seen in FIG. 3 this results in a very compact arrangement of the linear drive 9 and the clutch 24, with only a relatively small number of components.

Figure 4:
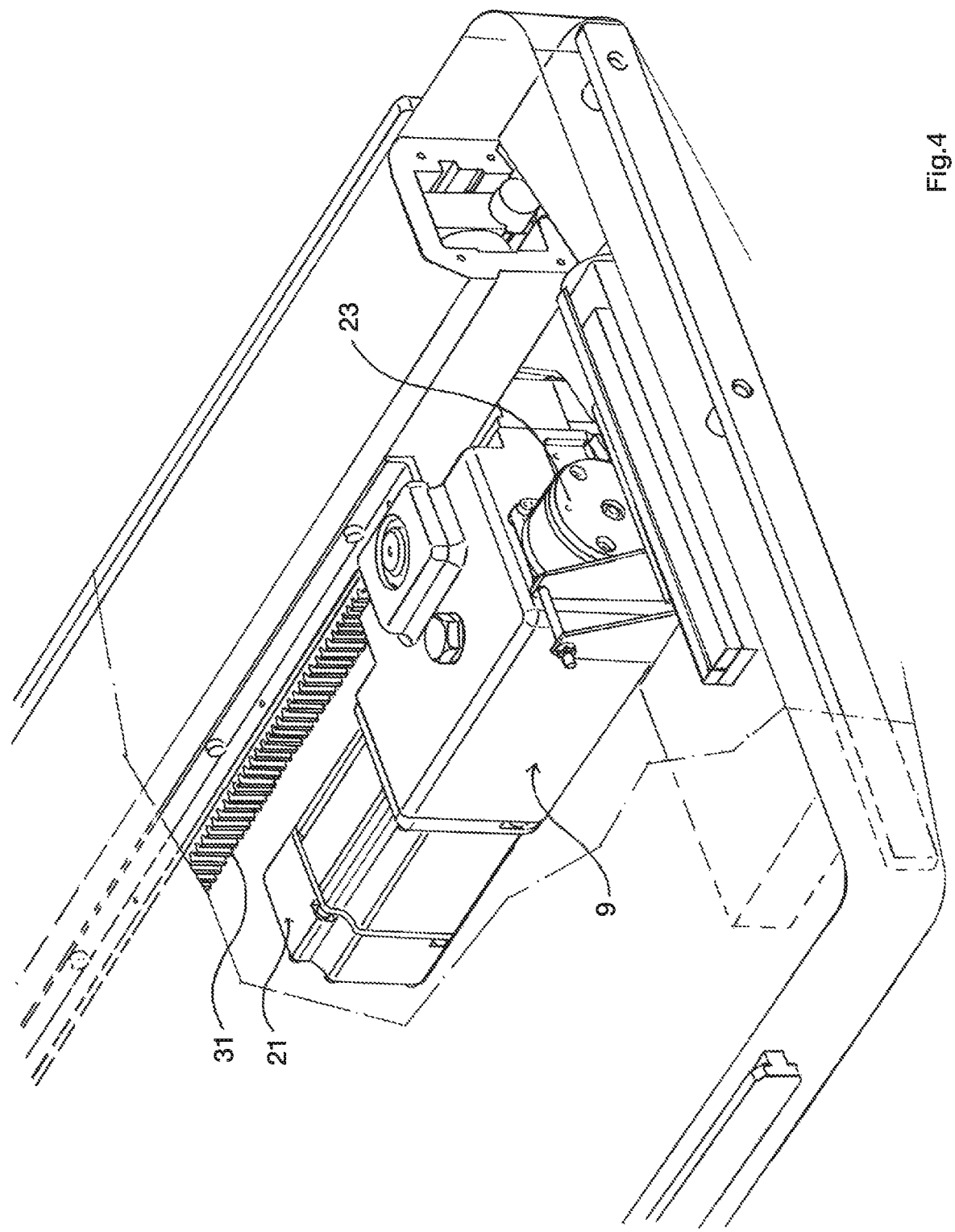
FIG. 4 is a perspective view of the compact linear drive according to FIG. 2 in the patient table and cooperating with a rack.

FIG. 4 shows a perspective view of the compact linear drive 9 according to FIG. 2 in the patient table 1 and cooperating with a rack 31 to move the table top 6 of the patient table 1 in the longitudinal direction. The table top (not shown in FIG. 4) is fixedly connected to and moves the rack 31. When the pinion shaft 27 is actuated (indirectly) by the motor 21, it rotates and its teeth will engage and move the rack 31.

Figure 5A:
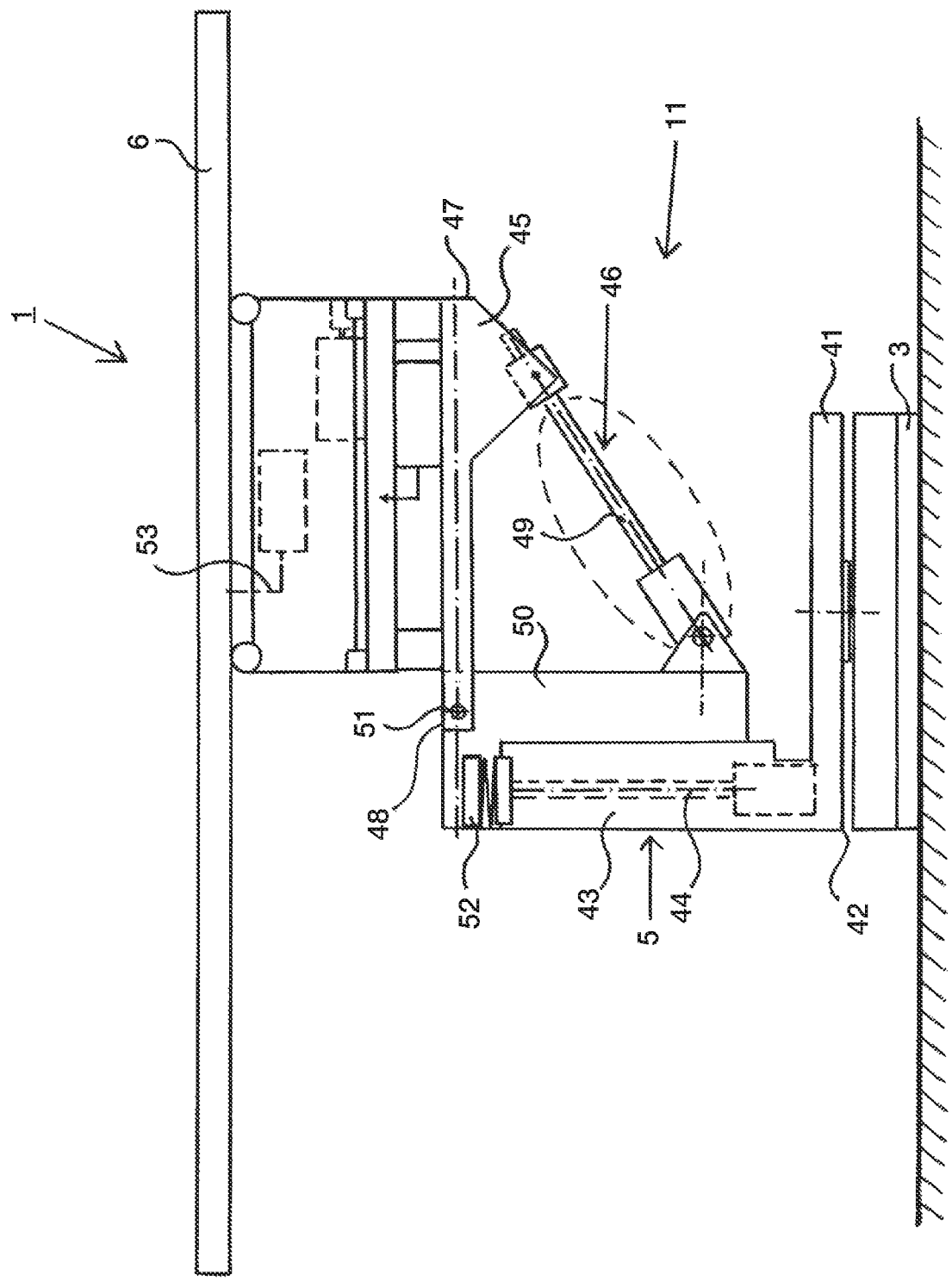
FIG. 5a is a schematic side view of a levelling device that is integrated in the patient support table of FIG. 1 in a neutral condition.

FIG. 5a shows a schematic side view of a leveling device 11 integrated in the patient support table 1 of FIG. 1 in a neutral condition. The leveling device 11 cooperates with components of the patient table 1 to, at least in use, continuously keep the table top 6 level, usually horizontal. The column 5 has a base plate 41 that is rotatably supported by the ring guide system 8. The axis of rotation of the column 5 extends through the centre of the ring guide system 8. Connected to an outer edge 42 of the base plate 41, is an upright hollow post 43 in which a linear drive piston-cylinder device 44 is enclosed. The piston-cylinder device 44 is able to vertically move the table top 6 with respect to the floor 2. On top of the piston-cylinder device 44 the piston-cylinder device 44 supports an intermediate part 50 to which a positioning table 45 is pivotably connected and extends horizontally above the base plate 41. Interposed between the piston-cylinder device 44 top and the positioning table 45 is a force sensor 52 that in use measures the force exerted to the piston-cylinder device 44 by the positioning table 45. At the bottom part of the intermediate part 50 a tilt actuator 46 is pivotably connected to the intermediate part 50, and extends to and is pivotably connected to an edge 47 of the positioning table 45 that is opposed to an edge 48 of the positioning table 45 that is supported by the cylinder 44. Thus, the positioning table 45 is supported at two outer edges 47, 48. The tilt actuator 46 has a piston-cylinder device 49 that can be extended and compressed to pivot the positioning table 45 about a horizontal pivot axis 51. The positioning table 45 supports several actuators that in use manipulate the table top 6 to, and maintain it in, the desired position as is depicted by means of arrows P4, P5 and P6 in FIG. 1, one of which is the compact linear drive 6 that has been discussed earlier herein in more detail. A longitudinal positioning sensor 53 disposed below the table top 6 and in a fixed position with respect to the positioning table 45 measures the longitudinal position of the table top 6 with respect to the positioning table 45.

FIG. 5b shows a schematic side view of the leveling device 11 of FIG. 5a, with the table top 6 supporting a patient 12 and longitudinally extended to an extreme (left) position. FIG. 5b clearly shows that the orientation of many components is changed compared to the same patient table 1 in the neutral position of FIG. 5a. The weight of the patient 12 and the position of the table top 6 tend the table top 6 to become off level in the absence of any corrective movements in the patient table 1. FIG. 5b. shows effects of the load of the table top 1 and corrections taken by the leveling device 11. One of the effects is that the arrangement of the table deflects under the weight of the patient 12. The extent to which the table deflects depends on several factors, amongst which the rotational stiffness of the table top 6 (which is a given constant for a specific patient table), the weight of the patient 12 and the (longitudinal) position of the centre of gravity of the load. Currently known systems correct the level of the table top independently of deflection of the table. For example by measuring the position of two reference points in the table top. This results in an inaccurate measurement and thus in an inaccurate corrective action which might result in the table top of the known patient table not being absolutely level (or exactly in a defined angle of inclination).

The leveling device 11 of the patient table 1 according to the current invention is able to make a more accurate correction. In use the controller of the leveling device 11 receives the actual force measured by the force sensor 52. This actual force is reduced with a result of a measurement of the force sensor 52 of an unloaded table top 6 and in the neutral position of the table top 6, which in fact is a constant value. The controller also receives the actual longitudinal position of the table top 6 measured by the longitudinal position sensor, i.e. the moment of the force working at the piston-cylinder device 44 top and is determined by force measurement at the position of the force sensor 52 times the longitudinal position. Those two values are multiplied and are then divided by the table support rotational stiffness (a constant) to result in a correction angle, and a corrective action is taken accordingly by the levelling device 11.

Figure 6A:
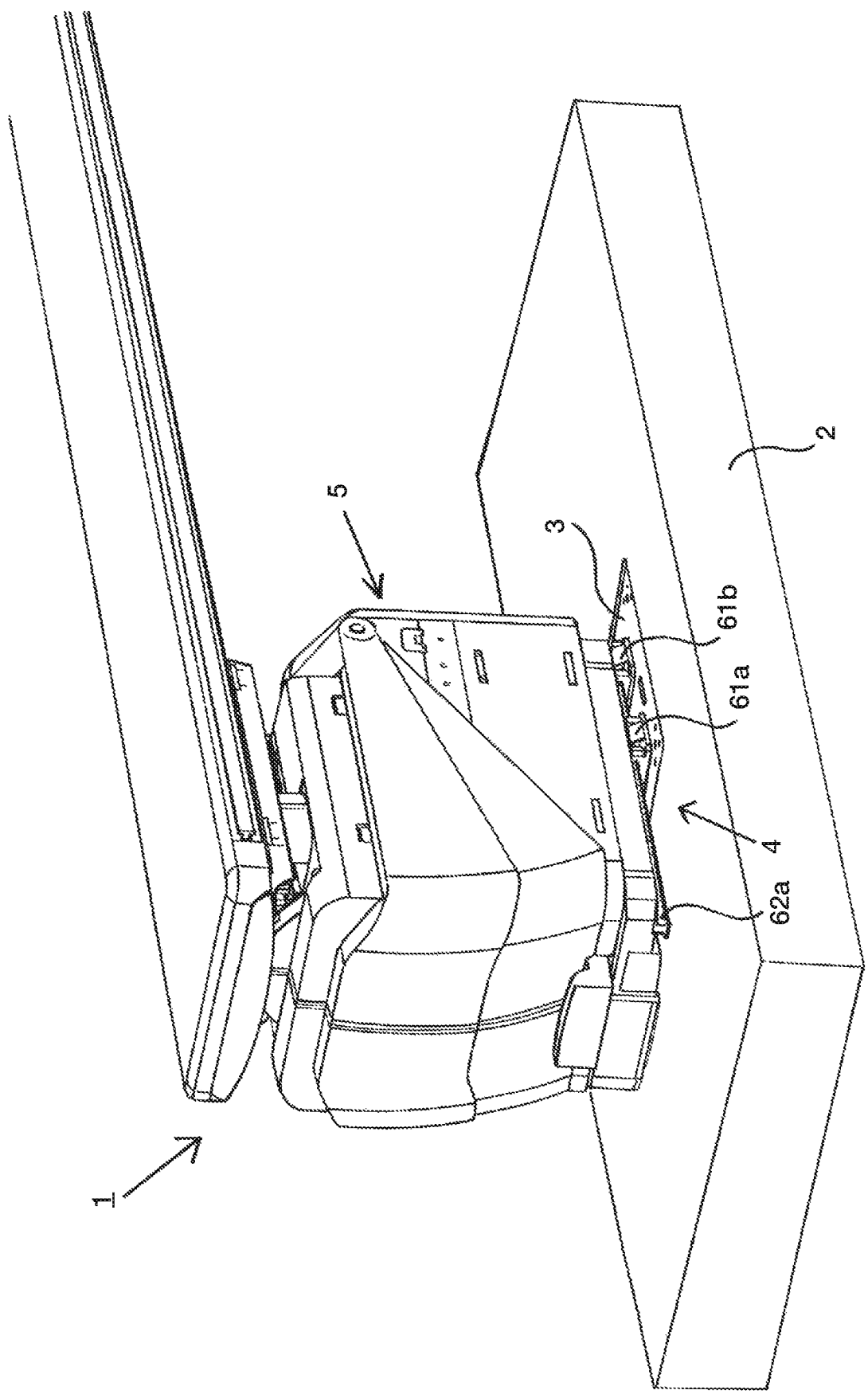
FIG. 6a is a perspective view of the guiding system of the patient support table of FIG. 1, with the column at a first location.

FIG. 6a is a perspective view of the guiding system 4 of the patient support table 1 of FIG. 1, with the column 5 at a first location. A lower front part of the housing 7 of the column 5 is taken away to make part of the guiding system 4 visible. A mounting plate 3 is fixedly mounted to the floor 2. Immovably attached to the mounting plate 3 are four guiding shoes 61a-61d, only two (61a, 61b) of which are visible in FIG. 6a. The two other guiding shoes are located at the opposite side of the mounting plate 3 which in FIG. 6a is hidden by the column 5. Mounted at the bottom of column 5 are two guide rails 62a, 62b, of which only guide rail 62a is visible in FIG. 6a. The guide rails 62a, 62b each extend through a pair of guide shoes 61a, 61b and 61c, 61c respectively. The column 5 is movable to the position shown in FIG. 6b, guided by the guide rails 62 that are guided by the guide shoes 61. This movement, in use, is actuated manually by pushing against the (foot side of) the top of the table or by pulling the (foot side of) the table 1.

In the installed position of the patient table 1 the mounting plate 3 is covered by a cover (not shown in FIGS. 6a, 6b). The lower part of the housing 7 of column 5 extends around the whole column 5, covering the guide rails 62 and close to the floor 2 and the cover. It will be clear to the reader that in the installed condition, no components visibly project to outside the housing of the column 5 or from the floor 2 (or the cover). This contributes to a safe, ergonomic environment for medical personnel and minimizes the risk of damage to the components of the column 5. The total distance between the outermost parts of the two guide shoes 61a, 61b that cooperate with a guide rail 62a is about ⅓th of the length of the rail. As a result a projection of the column 5 in the two extreme opposite positions "overlaps itself" over only this ⅓th of its length. This means that the column 5 can be moved over a distance of ⅔th of its own length.

Figure 7A:
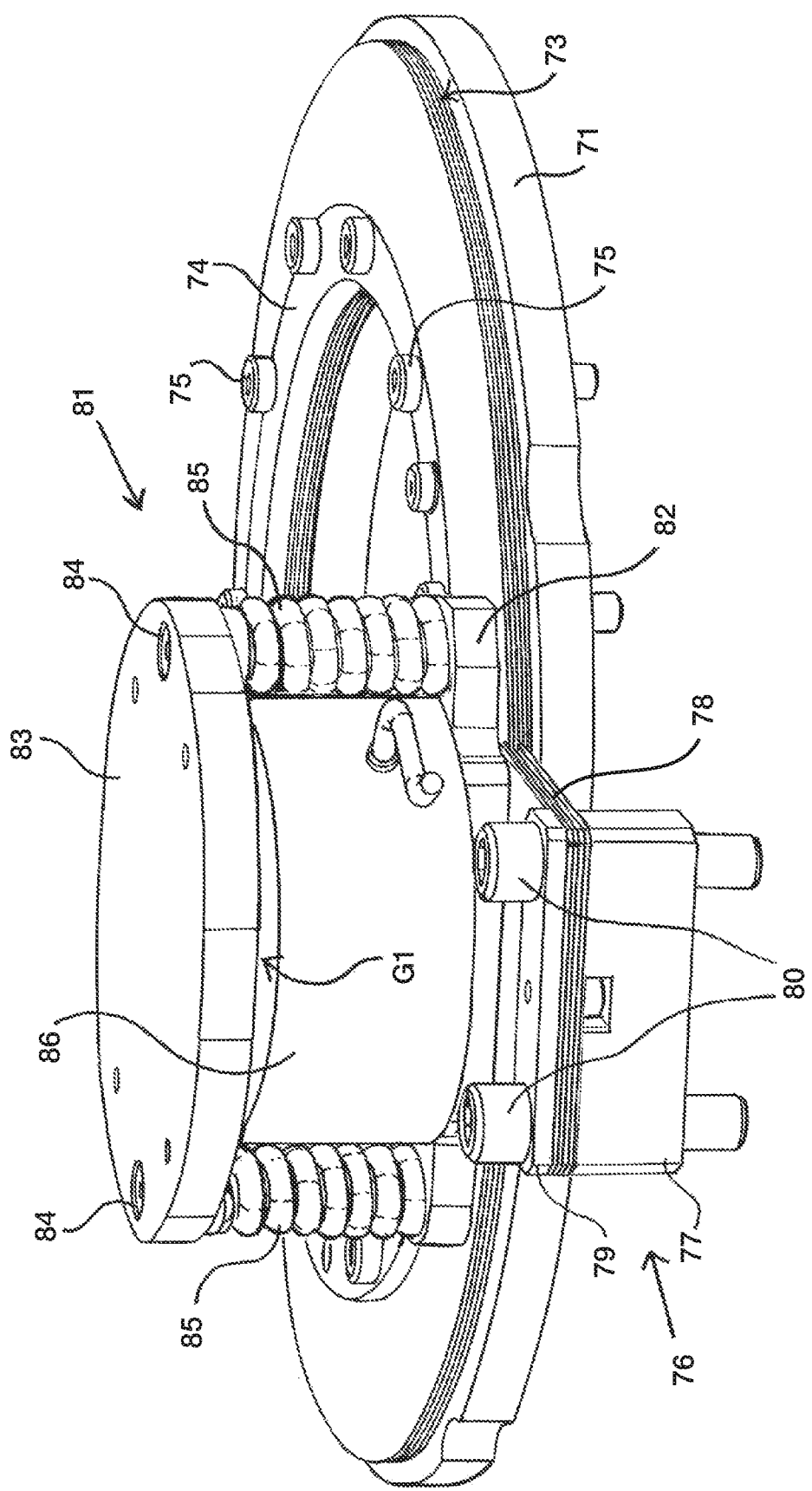
FIG. 7a is a perspective side view of a holding brake system of the patient support table of FIG. 1.

FIG. 7a shows a perspective side view of the holding brake system 13 of the patient support table 1 of FIG. 1. The holding brake system 13 is mounted to an annular ring guide system 8 that enables the column 5 to rotate about the substantially vertical central axis of a ring 71 of the ring guide system 8. The column 5 has a mounting plate 3 supporting a ring 71 that is fixedly mounted to the mounting plate 3. An annular mounting block 72 is attached to the immovable ring 71 and carries a number of static brake disks 73 that are stacked and clamped to the ring 71 by a clamping ring 74 and bolts 75. This will be elucidated in more detail in FIG. 8.

Figure 8:
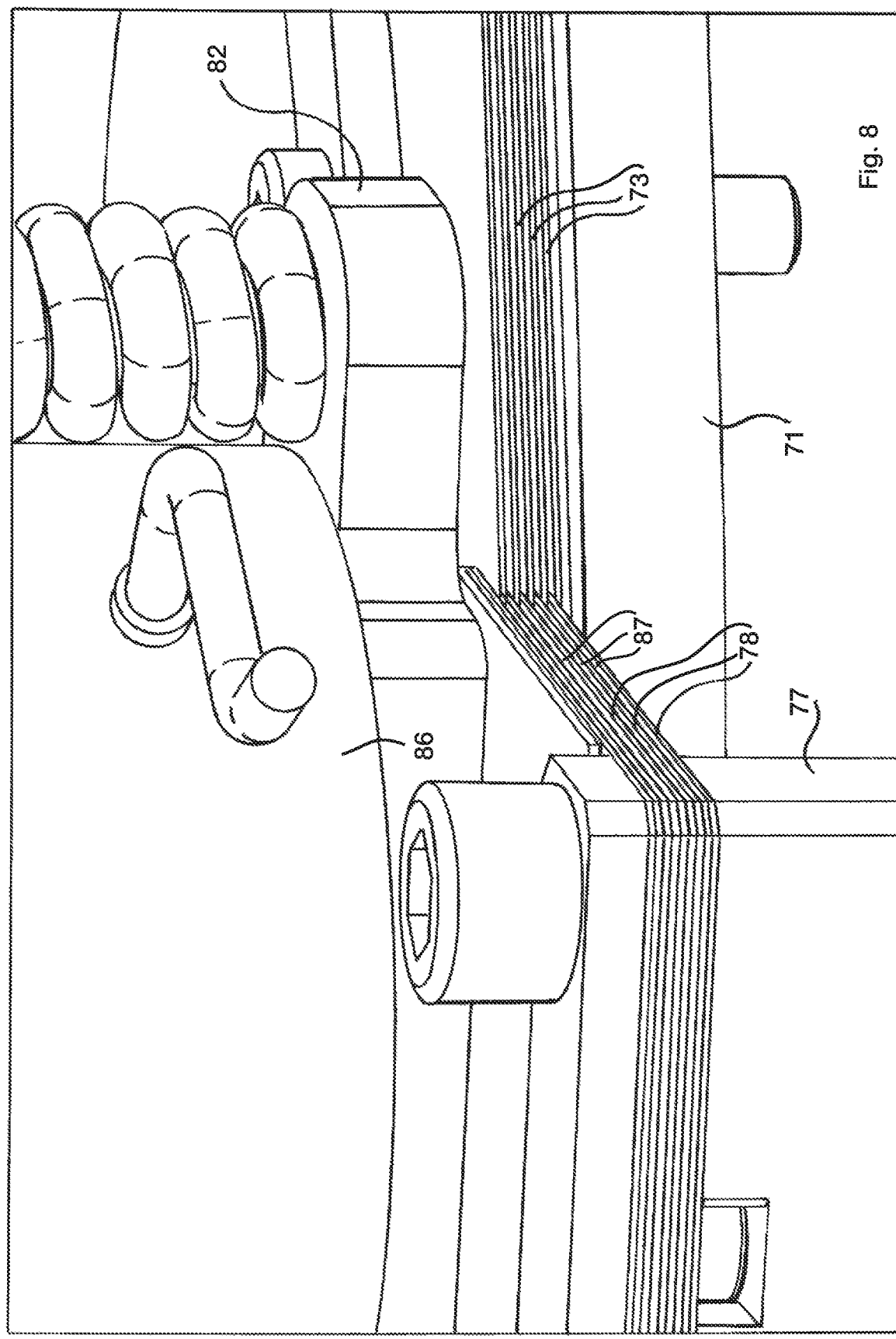
FIG. 8 is a detailed perspective side view, of part of the holding brake assembly of FIG. 7

A rectangular brake plate assembly 76 is mounted to the ring 71 and can move around the ring 71. The brake plate assembly 76 comprises a mounting block 77 that supports a number of stacked dynamic brake plates 78 that extend to outside the projection of the mounting block 77, all clamped together by a clamping strip 79 and inner hexagon socket screws 80. The rectangular brake plate assembly 76 is movably attached to the column 5 of the patient table 1. The brake plates 78 extend in the direction of the ring and between the brake disks 73. The brake disks 73 and brake plates 78 are in overlapping and alternating arrangement as can be seen in FIG. 8, which shows an enlarged detailed drawing of part of the holding brake system 13 which will be discussed later. When the brake plate assembly 76 moves around the ring 71, the brake plates 78 are maintained between the static brake disks 73. In this embodiment the upper brake plate 78, of course, is maintained in between the upper brake disk 73 and the pressure assembly 81.

Mounted above the overlapping parts of the brake disks 73 and the brake plates 78 is a pressure assembly 81 that is attached to the horizontal plate that is screwed onto the pivot frame connected to the column 5. The pressure assembly 81 has a bottom plate 82 and a top plate 83 which are mutually connected by pins 84. Helical compression springs 85 are arranged around the pins 84 and drive the bottom plate 82 away from the top plate 83. Arranged in the centre of the pressure assembly 81 is an electromagnet 86 that is fixed to the bottom plate 82.

FIG. 8 shows a part of the holding brake system 13 in more detail. The mounting block 77 supports the brake plates 78 that are spaced apart by spacers 87 positioned between adjacent brake plates 78. A clamping strip 79 on top of the stack of brake plates 78 clamps the brake plates 78 together and to the mounting block 77. The brake plates 78 (except the upper one) extend to in between brake disks 73 that are attached to the static ring 73 mounted to the mounting plate 3 in the lower part of the patient table 1, and which is not rotatable with respect to the floor. The bottom plate 82 of the pressure assembly 81 is located above the overlapping brake plates 78 and disks 73.

In use, in the non-powered condition of the electromagnet 86 as shown in FIG. 7a, the bottom plate 82 of the pressure assembly 81, together with the electromagnet is driven away from the top plate 83 by the helical compression springs 85. A gap G1 is present between the electromagnet 86 and the top plate 83. The bottom plate 82 exerts a normal force to the alternatingly stacked brake disks 73 and brake plates 78. In this condition of the pressure assembly 81 the mutually facing surfaces of the brake disks 73 and plates 78 act as friction surfaces. The number of friction surfaces can be chosen as desired (or required) by adding/removing brake plates 78 or brake disks 73 and amounts nine in the arrangement of FIG. 8. A relatively small normal force is required to generate a relatively large holding force of the holding brake system 13. Thus, if the electromagnet 86 is not powered, the brake plates 78 that are rotatable with respect to the ring 71 are trapped and kept immovably in position by the static brake disks 73.

Figure 7B:
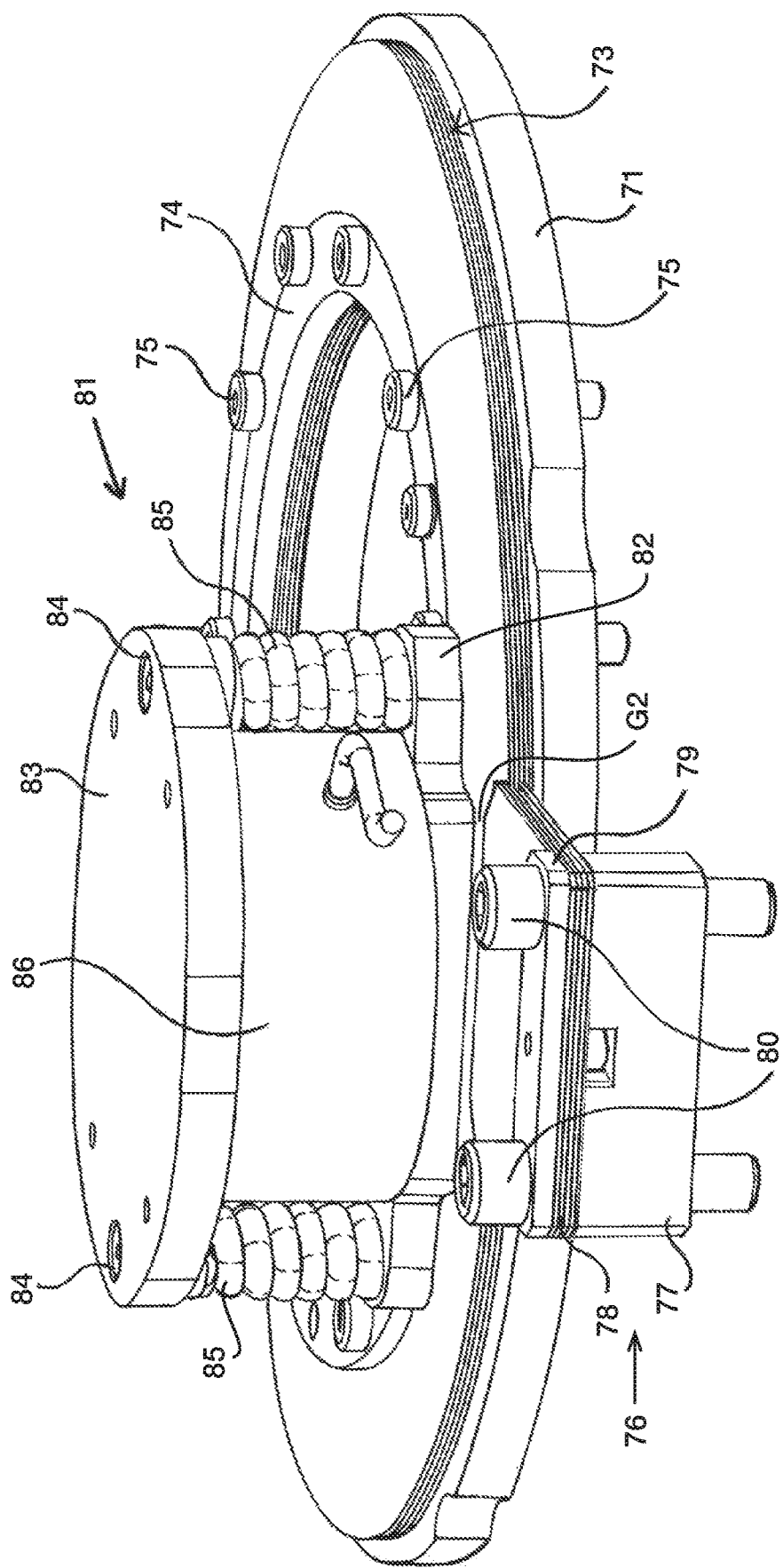
FIG. 7b is a perspective side view of a holding brake system of the patient support table of FIG. 1.

If the electromagnet 86 is powered, as shown in FIG. 7b, the electromagnet 86, together with the bottom plate 82, pulls itself to the top plate. No gap (G1) is present between the electromagnet 86 and the top plate 83. Instead, a gap G2 is present between the bottom plate 82 and the upper brake disk 73. No normal force is exerted to the mutually overlapping brake disks 73 and brake plates 76 and the brake plates 78 are able to move freely with respect to the brake discs 73 and the ring without (substantial) friction between the friction surfaces.

In the figures and in the description thereof only one preferred embodiment of a patient table according to the current invention is shown and described. It will be clear, however, that many modifications, that may or may not be obvious to for the skilled person, may be made to the patient table within the scope of the invention defined in the following claims. It is possible, for example, to use a closed spring solution instead of a normally closed permanent magnet in the brake as a clutch in the compact linear actuator. The compact linear actuator could be applied in other drive arrangements in the patient table. The pinion could also be in engagement with a toothed belt, which would enable to arrange the actuator at a different location. The worm gear could be replaced by an angular arrangement of a different type that a worm gear arrangement.

The second to fifth point of view may be incorporated independently from each other, and in particular independent from the invention from a first point of view, which different points of view have been described above. In particular, the protection sought is defined in the amended claims, and relates in particular to the first point of view. The second to fifth point of view may be described by the following clauses.

Second Point of View

Clause a.1. Patient support system arranged to position and support a patient lying on a support system, for example at X-Ray Systems, especially Cardio/Vascular systems, comprising a frame that, in use, is mounted to a floor, an upright column mounted to the frame and supporting a substantially rectangular table top defining a plane and which is movable in said plane with respect to the column to accommodate a patient, and a controlling device with a motor and a gear for moving the table top to a desired position, characterised in that the gear is a hollow axis angular gear.

Clause a.2. Patient support system according to clause a.1, wherein the motor has an output shaft that is at the same time an input shaft of an angular gear wheel of the angular gear.

Clause a.3. Patient support system according to clause a.2, wherein the angular gear input shaft directly engages and rotates the angular gear wheel when actuating the movement of the table top.

Clause a.4. Patient support system according to one or more of the clauses a.1-a.3, wherein an output pinion is at least partially enclosed in the hollow angular gear axis, which output pinion in use is actuated by the angular gear.

Clause a.5. Patient support system according to one or more of the clauses a.1-a.4, wherein the output pinion engages a rack that is connected to the table top, to convert a rotary movement of the motor to a linear movement of the table top.

Clause a.6. Patient support system according to one or more of the clauses a.1-a.5, comprising a clutch that is switchable between an operational condition wherein the angular gear is in driving engagement with the output pinion and an non-operational position in which the angular gear is not in driving engagement with the output pinion.

Clause a.7. Patient support system according to clause a.6, wherein, in the non operational position of the gear, the pinion is freely rotatable.

Clause a.8. Patient support system according to clause a.6 or a.7, wherein the clutch is an electromechanical clutch.

Clause a.9. Patient support system according to one or more of the clauses a.1-a.8, wherein a safety brake is provided to lock the controlling device when no movement of the table top is allowed.

Clause a.10. Controlling device for use in a medical device, especially in a patient support system, having a movable table top, and comprising a motor and a gear for moving the table top to a desired position, wherein the gear comprises a hollow axis angular gear.

Clause a.11. Use of a controlling device according to clause a.10, especially in a patient support system according to any of the clauses a.1-a.9.

Third Point of View

Clause b.1. Patient support system arranged to position and support a patient lying on the support system, for example at X-Ray systems, especially Cardio/Vascular systems comprising a frame that, in use, is mounted to a floor, an upright column mounted to the frame and supporting a substantially rectangular table top defining a plane and which is movable longitudinally in said plane with respect to the column to accommodate a patient, the patient support system comprising a guiding device developed to guide the column from a first position with respect to the floor to a second position with respect to the floor, characterised in that in use the guiding device is arranged to guide the column in a rectilinear path between the first and the second position.

Clause b.2. Patient support system according to clause b.1, wherein the guiding device comprises at least one first, relatively long guiding element connected to the column and at least one second, relatively short guiding element mounted to the floor, the first and second guiding elements being in mutually guiding engagement.

Clause b.3. Patient support system according to clause b.1 or b.2, comprising at least two second, relatively short guiding elements that are spaced apart and aligned in the guiding direction and both being in guiding engagement with the at least one first guiding element.

Clause b.4. Patient supporting device according to clause b.3, wherein the at least two second guide elements are mutually connected by means of a mounting element.

Clause b.5. Patient supporting device according to one or more of the clauses b.1-b.4, characterised in that the guiding device comprises at least two guiding mechanisms arranged in parallel.

Clause b.6. Patient supporting device according to clause b.5, wherein the at least two guiding mechanisms are mutually connected by means of a mounting plate.

Clause b.7. Patient supporting device according to one or more of the preceding clauses b.2-b.6, wherein the at least one first guiding element is a guide rail that extends substantially over the full length at the bottom of the column.

Clause b.8. Patient supporting device according to one or more of the preceding clauses b.1-b.7, wherein the at least one second guiding element is a guiding shoe.

Clause b.9. Patient supporting device according to one or more of the preceding clauses b.1-b.8, wherein the at least one second guide element, or, when dependent of clause b.3 or b.4, the mutually aligned second guiding element, engaging the same first guide element, extend(s) over a total distance of no more than two-third, preferably no more than one half and more preferably no more than one third of the length of the column in the guiding direction.

Clause b.10. Patient supporting device according to one or more of the preceding clauses b.1-b.9, wherein the column comprises at least one locking mechanism to lock the column in at least each of the first and second positions.

Clause b.11. Patient supporting device according to one or more of the preceding clauses b.1-b.10, the patient supporting device comprising a position sensor that, in use, detects the position of the column with respect to the floor.

Clause b.12. Patient supporting device according to one or more of the preceding clauses b.2-b.11, wherein the at least one second guide element is mounted at least partly sunk in the floor.

Clause b.13. Patient supporting device according to one or more of the preceding clauses b.1-b.12, wherein the table top is also movable transversely or vertically.

Clause b.14. Patient supporting device according to one or more of the preceding clauses b.1-b.13, wherein the column comprises at least one holding mechanism to hold the column in any (indiscrete) position.

Clause b.15. Guiding device developed to guide a column of a patient table that is attached to a floor from a first position with respect to the floor to which the patient table is attached to a second position with respect to the floor, wherein, in use, the guiding device is arranged to guide the column in a rectilinear path between the first and the second position.

Clause b.16. Use of a guiding device according to clause b.15, preferably arranged in a patient support system according to any of the clauses b.1-b.14.

Fourth Point of View

Clause c.1. Patient support system arranged to position and support a patient lying on the support system, for example at X-Ray systems comprising a frame that is, in use, mounted to a floor and an upright column that is mounted to the frame and is movable with respect to the frame, the patient support system comprising a holding brake device to hold the column in a set position, the holding brake device comprising at least one static component and at least one movable component, movable with the column and with respect to the at least one static component in a reference plane, the holding brake device being arranged to prevent the at least one movable component to move parallel to the reference plane in an activated condition of the holding brake device and being arranged to allow the at least one movable component to move parallel to said reference plane in an inactivated condition of the holding brake device, furthermore comprising at least two first, static brake plates extending from the at least one static component, parallel to the reference plane, and, seen perpendicularly to the reference plane, side by side, and at least two second movable brake plates extending from the at least one movable component, parallel to the reference plane, and at least in the activated condition of the holding brake device partly overlapping the first brake plates, wherein the at least two first and at least two second brake plates, at least in the activated position of the holding brake device, are arranged alternatingly, and comprising a pressure assembly that applies a normal force to the brake plates to activate the brake device and releases said normal force to inactivate the brake device.

Clause c.2. Patient support system according to clause c.1, wherein a brake plate is made of metal.

Clause c.3. Patient support system according to clause c.1 or c.2, comprising at least three, preferably at least four, first brake plates.

Clause c.4. Patient support system according to clause c.1, c.2 or c.3, comprising at least three, preferably at least four, second brake plates.

Clause c.5. Patient support system according to one or more of the preceding clauses c.1-c.4, wherein a surface of an outer brake plate facing away from the other brake plates is covered with a resilient layer.

Clause c.6. Patient support system according to clause c.5 wherein the resilient layer is made of rubber.

Clause c.7. Patient support system according to one or more of the preceding clauses c.1-c.6, wherein the thickness of the brake plates is in the range of 0.02-4.0 mm.

Clause c.8. Patient support system according to one or more of the preceding clauses c.1-c.7, wherein two adjacent first brake plates and/or two adjacent second brake plates are spaced apart.

Clause c.9. Patient support system according to one or more of the preceding clauses c.1-c.8, wherein a spacer is arranged between two adjacent first brake plates and/or between two adjacent second brake plates.

Clause c.10. Patient support system according to one or more of the preceding clauses c.1-c.9, wherein the pressure assembly comprises an electromagnetic switch.

Clause c.11. Patient support system according to one or more of the preceding clauses c.1-c.10, wherein the pressure assembly comprises a helical pressure spring.

Clause c.12. Patient support system according to one or more of the preceding clauses c.1-c.11, wherein the first, static brake plates are ring shaped and are arranged such that a rotation axis of the movable part of the patient support table extends perpendicularly through the centre of the ring shaped static brake plates.

Clause c.13. Patient support system according to one or more of the preceding clauses c.1-c.12, wherein the movable part of the patient support system is arranged to be translatable, and wherein the brake plates are arranged rectilinear.

Clause c.14. Patient support system according to one or more of the preceding clauses c.1-c.13, wherein the path of movement of the movable part of the medical device is complex, wherein the first, static brake plates extend at least substantially correspondingly to the path of movement.

Clause c.15. Holding brake device for use in a patient support system and comprising at least one static component and at least one movable component, movable with respect to the at least one static component in a reference plane, the holding brake device being arranged to prevent the at least one movable component to move parallel to the reference plane in an activated condition of the holding brake device and to allow the at least one movable component to move parallel to said reference plane in an inactivated condition of the holding brake device, at least two static brake plates extending from the at least one static component and parallel to the reference plane and, seen perpendicularly to the reference plane, side by side and apart, and at least two second movable brake plates extending from the at least one movable component and parallel to the reference plane, and at least in the activated condition of the holding brake device partly overlapping the first brake plates, wherein the first and second brake plates are arranged alternatingly, and a pressure assembly that applies a normal force to the brake plates to activate the brake device and releases said normal force to inactivate the brake device.

Clause c.16. Use of a patient support system according to one or more of clauses c.1-c.14 and/or a holding brake according to clause c.15.

Fifth Point of View

Clause d.1. Patient support system arranged to position and support a patient lying on the support system, for example at X-Ray systems, comprising a frame that is, in use, mounted to a floor, an upright column mounted to the frame and supporting a substantially rectangular table top defining a plane and which is movable in said plane with respect to the column to accommodate and position a patient, and a controlling device with a motor and a gear assembly for moving the table top to a desired position and a clutch for activating and deactivating the gear assembly, characterised in that the controlling device comprises an electromechanical brake as the clutch.

Clause d.2. Patient support system according to clause d.1 wherein the electromechanical brake is integrated in the gear assembly.

Clause d.3. Patient support system according to clause d.1 or d.2, wherein the electromechanical brake comprises a coiled magnet and a first friction element that is movable with respect to a second friction element of a component to be switched between a locked condition an a released condition, between an operational position wherein the first and second friction elements are mutually in engagement and a non operational position wherein the first and second friction surfaces are disengaged.

Clause d.4. Patient support system according to clause d.3, wherein the clutch is arranged to be in the locked position when the clutch is not powered.

Clause d.5. Patient support system according to clause d.3 or d.4, wherein the second friction element is comprised in, or fixed to, an actuation part of the gear assembly.

Clause d.6. Patient support system according to one or more of the preceding clauses d.1-d.5, wherein the electromechanical brake is arranged in parallel with a hollow axis angular gear, and wherein the electromechanical brake also comprises a hollow axis, which is at least substantially aligned with the hollow axis of the gear wheel.

Clause d.7. Patient support system according to one or more of the preceding clauses d.1-d.6, wherein a rotary electrical feedthrough is provided, preferably embodied as a slipring.

Clause d.8. Patient support system according to one or more of the preceding clauses d.1-d.7, wherein the gear assembly is developed to linearly move the table top in the rectangular plane of the table top.

Clause d.9. Patient support system according to clause d.8, wherein the gear assembly is developed to linearly move the table top longitudinally in the rectangular plane of the table top.

Clause d.10. Controlling device for use in a medical device, especially a patient support system according to any of clauses d.1-d.9, having a table top the controlling device comprising a motor and a gear assembly for moving the table top to a desired position, a clutch for activating and deactivating a gear assembly to actuate movement of the table top and a brake to lock the table top in the desired position, characterised in that the controlling device comprises an electromechanical brake as the clutch.

Clause d.11. Use of a controlling system according to clause d.10, preferably in a medical device, especially a patient support system according to any of clauses d.1-d.9.

The invention claimed is:

1. A support system comprising
    a floor-mountable frame;
    an upright column mounted to the frame;
    a load-supporting table top supported on and movable longitudinally relative to the column, to a longitudinal position;
    at least one tilt actuator adjustably connected to the table top; and
    a control device comprising:
        an inclination measuring device;
        a data storage;
        a processing unit;
        a force sensor for determining the load supported by the table top; and a position sensor for determining the longitudinal position of the table top, the control device configured to:
- determine, using the position sensor, the longitudinal position of the table top with respect to a reference,
- calculate an expected flexing of the table top based on the longitudinal position of the table top, a load supported by the table top, and a rotational stiffness of the table top,
- calculate, based on the calculated expected flexing, a set point for the at least one tilt actuator for actuating the at least one tilt actuator to move the table top or maintain the table top at a set tilted position, and
- actuate, based on the calculated set point, the at least one tilt actuator to move or maintain the table top at the set tilted position.

2. The support system according to claim 1, wherein the set tilted position is a substantial horizontal position.

3. The support system according to claim 1, further comprising
- a vertical support in the column; and
- a positioning table supported by the vertical support and supporting the table top,
- the positioning table comprising motor arrangements for positioning the table top with respect to the column.

4. The support system according to claim 3, wherein the positioning table has a first end attached to the vertical support, and an opposite second end at or near which the tilt actuator is supportingly connected.

5. The support system according claim 3, wherein the vertical support has a bottom part and wherein the tilt actuator comprises a linear drive extending from the bottom part to the positioning table.

6. The support system according to claim 3, wherein the force sensor is located between a top of the vertical support and the positioning table.

7. The support system according to claim 1 wherein the table top is made of a material that minimizes influence on X-Ray imaging of a patient.

8. The support system according to claim 1, wherein the force sensor is arranged for determining the load by measuring motor current of vertical displacement of the table top.

9. The support system of claim 1, wherein the support system is a system for positioning a patient in an X-ray system.

10. The support system of claim 1, wherein the control device is further configured to:
- determine an actual torque value based on the load supported by the table top, and
- calculate the set point for the at least one tilt actuator based on dividing the actual torque value by the rotational stiffness of the table top.

11. The support system of claim 10, wherein the control device is further configured to:
- determine the actual torque value based on multiplying the load supported by the table top by the table top longitudinal position with respect to the reference.

* * * * *